(12) United States Patent
Steliou

(10) Patent No.: US 6,316,652 B1
(45) Date of Patent: Nov. 13, 2001

(54) DRUG MITOCHONDRIAL TARGETING AGENTS

(76) Inventor: Kosta Steliou, Boston University Department of Chemistry 590 Commonwealth Ave., Boston, MA (US) 02215

(*) Notice: Subject to any disclaimer, the term of this patent is extended or adjusted under 35 U.S.C. 154(b) by 0 days.

(21) Appl. No.: 08/468,844

(22) Filed: Jun. 6, 1995

(51) Int. Cl.⁷ .................. C07F 1/10; C07F 1/12; C07F 15/00; C07F 3/00
(52) U.S. Cl. .................. 556/42; 549/3; 514/184; 514/189; 514/492; 514/493; 514/494; 514/495; 514/501; 514/502; 514/505; 556/136; 556/43; 556/57; 556/58; 556/45; 556/46; 556/138; 556/140; 556/110; 556/112; 556/118; 556/121
(58) Field of Search .................. 549/3; 556/136, 556/42, 43, 57, 58, 45, 40, 138, 140, 110, 112, 118, 121; 514/184, 189, 492, 493, 494, 495, 499, 501, 502, 505

(56) References Cited

U.S. PATENT DOCUMENTS

| | | | |
|---|---|---|---|
| 4,742,081 | 5/1988 | Stracher et al. | 514/547 |
| 4,866,040 | 9/1989 | Stracher et al. | 514/17 |
| 5,008,288 | 4/1991 | Stracher et al. | 514/535 |
| 5,318,962 | * 6/1994 | Khokhar et al. | 514/184 |
| 5,348,950 | * 9/1994 | Hata et al. | 549/3 X |
| 6,054,271 | * 4/2000 | Tsien et al. | 549/3 X |

OTHER PUBLICATIONS

R. B. Weiss et al., "New Cisplatin Analogues in Development: A Review" *Drugs* 46:360–377 (1993).

M. Gordon et al., "Review of Platinum Anticancer Compounds" *J. Med.* 24: 209–265 (1993).

L. S. Hollis, "New Approaches to the Design of Platinum Antitumor Agents" *Platinum and Other Metal Coordination Compounds in Cancer Chemotherapy*, 115–125 (S. B. Howell, ed. 1991).

R. B. Fram, "Cisplatin and Platinum Analogues: Recent Advances" *Curr. Opin. Oncology* 4: 1073–1079 (1992).

W. J. Brouillette et al., "Synthesis and Enzymatic Evaluation of Conformationally Defined Carnitine Analogs" *J. Org. Chem*.59: 4297–4303 (1994).

S. V. Pande et al., "Carnitine–Acylcarnitine Translocase Catalyzes an Equilibrating Unidirectional Transport As Well" *J. Biol. Chem.* 255: 2994–3001 (1980).

M. S. R. Murthy et al., "Mechanismof Carnitine Acylcarnitine Translocase–catalyzed Import of Acylcarnitines into Mitochondria" *J. Biol. Chem.* 259: 9082–9089 (1984).

H.R. Brady et al., "Mitochondrial Injury An Early Event in Cisplatin Toxicity to Renal Proximal Tubules"*Am J Physiol*, vol. 258, No. 5 part 2, 1990, pp. F1181–F1187.

D.S. Choi et al, "The Acute Neprohtotoxicity of Cis Diamminedichloroplatinum–II in Rats An Ultrastructural Observation" *Seoul J Med.*, vol. 25, No. 2, 1984, pp. 168–185.

A.F. Noels et al, "Novel platinum(II)–diaminobiotin complexes. Their systhesis and characterization" *Bull. Soc. Chim. Belg.*, vol. 100, No. 7, 1991, pp. 497–502.

IT 1 169 460 B (Sigma Industrie Farmacuetiche Riunite S.P.A.), May 27, 1987, p. 2, line 19; p. 3, line 15; table 4, p. 13.

J. E. Christman et al., "Study of the Selective Cytotoxic Properties of Cationic Lipophilic Mitochondrial–Specifie Compounds in Gynological Malignancies" Abstract, table 1; paragraph: discussion: figure 8.

Im Huxham et al., "Intracellular localization of anticancer therapeutic compounds using electron spectroscopic imaging as a tool to investigate mecanisms of drug targeted cancer therapy" Database Cancerlit Cancer Institute, Bethesda, Md. AN NCI: 96616469; and *Br. J. Cancer*, vol. 71, Suppl. 24, p. 12, 1994.

M. M. Jones et al., "Control of the nephrotoxicity of cisplatin by clinically used sulfur–containing compounds" Abstract; Figure1; Tables 1–4.

* cited by examiner

*Primary Examiner*—Paul F. Shaver
(74) *Attorney, Agent, or Firm*—David Prashker

(57) ABSTRACT

The invention relates to novel targeting drug agents that are targeted for entry into the mitochondria. More specifically, the agents are cisplatin derivatives called mitoplatins which are useful as anti-tumor agents. Mitoplatins are named for their targeting to the mitochondrial DNA via the carnitine-acylcarnitine translocase system. The invention also relates to methods of synthesizing mitoplatins, compositions of matter containing mitoplatins and methods of using the mitoplatins.

71 Claims, 11 Drawing Sheets

14

15

1　　3　4　　　6　8　10　12

2　　5　　　7　9　11　　13

16

17

DRUG MITOCHONDRIAL TARGETING AGENTS

BACKGROUND OF THE INVENTION

1. Field of the Invention

The present invention relates to novel drug targeting agents. More particularly, the invention relates to drug agents having a unique targetor which affords the agents access to mitochondria via the acylcarnitine translocase system. These novel drug targeting agents are useful in the treatment of cancer, arthritis, skin, metabolic (i.e. diabetes), immunological (i.e. AIDS, tissue rejection) and neurodegenerative disorders (i.e. dementia, Alzheimer's disease). The agents also have useful diagnostic and monitoring applications.

2. Description of the Prior Art

Transport of exogenous substances such as therapeutic or diagnostic agents across cell membranes into mitochondria is highly selective and tightly controlled by two separate membrane barriers. Access to mitochondria is achieved through the acylcarnitine translocase system. L-Carnitine (γ-amino-(R)-β-hydroxybutyric acid trimethylbetaine), acting in concert with mitochondrial acyltransferases, $CPT_o$ and $CPT_i$, and an enzyme known as the carnitine acylcarnitine translocase, facilitates transport of fatty acids through the inner membrane of the mitochondria and into the matrix where the energy yielding fatty acid β-oxidation, as well as ketone body synthesis takes place.

Consequently, L-camnitine is an essential natural compound and is found in both plant and animal tissues. Though there is a propensity in vertebrates for L-carnitine to concentrate in heart and muscle tissue, both of which depend heavily on fatty acid oxidation for the production of energy, carnitine also concentrates 10 to 100 fold higher in the liver, kidney, brain, testes and epididymis than in plasma. Thus, a variety of diseases can be targeted with a caritine delivery system.

While it has been known for some time that carlitine mediates the energy requirements of a cell, this property has not been taken advantage of in therapeutic applications. Indeed, only as recently as 1991 has interest in this natural product as a targeting ligand of pharmaceutical agents surfaced. U.S. Pat. Nos. 4,742,081, 4,866,040 and 5,008,288 teach the use of carnitine-coupled pharmaceuticals to deliver those pharmaceuticals to cardiac and skeletal muscle. Specifically, these patents contemplate coupling carnitine to protease inhibitors and cardioactive compounds such as pepstatin, leucylarginal, procainamide, quinidine, and propranalol. Not contemplated however, is the use of carnitine as a targeting ligand of antitumor, antiemitic, or antiartritis agents.

Neoplastic disorders constitute a major health problem in the world today. Few antineoplastic agents have the dual beneficial properties of both efficacy and reduced toxicity The vast majority of antineoplastic agents currently in use are generally both relatively non-tumor specific, as well as toxic to the individual being treated. For example, typical toxicities associated with antitumor therapeutic agents include immune suppression, bone marrow depression, alopecia, and a host of other unwanted side effects. The key in identifying beneficial antineoplastic agents is in isolating agents which are capable of inhibiting neoplastic growth without adversely affecting normal cell growth.

Cisplatin has been known since 1845 when it was first named Peyrone's salt or Peyrone's chloride and used primarily in the development of coordination theory. However, it was not known to have cytotoxic effects until the serendipitous work of Barnett Rosenberg in 1962. By the end of the 1970's cisplatin had become a key drug in the treatment of certain germ cell cancers. In the past 20 years, cisplatin's antitumor efficacy has expanded to include ovarian and testicular tumors, oropharyngeal carcinoma, bronchogenic carcinoma, cervical carcinoma, melanoma, lymphoma, bladder carcinoma, neuroblastoma and others. The major obstacles to the efficacy of cisplatin in the treatment of cancer are poor water solubility, resistance to the drug and toxicity. Common side effects of cisplatin include nephrotoxicity (kidney damage), ototoxicity (damage to the nerves or organs involved in hearing and balance), myelosuppression (bone marrow suppression) resulting in leukopenia (depletion of leukocytes from the blood), neutropenia (depletion of neutrophils), or thrombocytopenia (depletion of platelets), neurotoxicity (damage to peripheral nerves), and a marked emesis (nausea and vomiting). Side effects occasionally include serum electrolyte imbalances, ocular toxicity (damage to the optic neurons), vascular toxicities, and cardiac abnormalities. Anaphylactic shock may also occur within minutes of administration in patients that are allergic to platinum (generally through occupational exposure).

Since the initial report on the anti-neoplastic properties of cisplatin, thousands of analogs have been made in an attempt to alleviate these adverse properties of cisplatin. Although roughly thirteen of these analogs have been tested in clinical trials, only one analog, carboplatin, has been a definite improvement over cisplatin. Carboplatin has a similar antitumor profile a, cisplatin. However, carboplatin causes less emesis, and is less toxic to the eighth cranial nerve, the peripheral nerves, and renal tubules. The decreased nephrotoxicity allows carboplatin to be administered on an outpatient basis. Bone marrow suppression is the dose-limiting side effect of carboplatin. The structures of cisplatin and carboplatin are as follows:

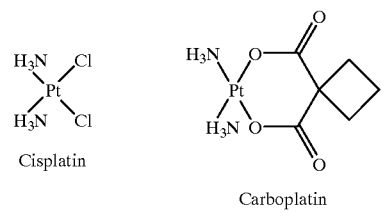

Cisplatin

Carboplatin

In spite of these disadvantages, the unparalleled clinical importance of cisplatin and carboplatin in the treatment of many types of solid tumors justifies the effort to find a therapeutically more palatable analog.

The cisplatin analogs that have been studied to date are described in Raymond B. Weiss & Michaele C. Christian, New Cisplatin Analogues in Development, *Drugs*, 46(3): 360–377 (1993); Maxwell Gordon & Sandra Hollander, Review of Platinum Anticancer Compounds, *J. Med.* 24(4–5); 209–265 (1993); and L. Steven Hollis, New Approaches to the Design of Platinum Antitumor Agents, *Platinum and Other Metal Coordinating Compounds in Cancer Chemotherapy*, 115–125 (Stephen B. Howell, ed. 1991), all of which are incorporated herein by reference.

Cisplatin and carboplatin are known to exhibit their anti-cancer activities by interfering with DNA replication. Though not yet fully elucidated, the currently accepted mechanism by which cisplatin interacts with chromosomal (nuclear) DNA is as follows: In die presence of DNA, exchange of a labile leaving group leads to preferential, though not exclusive, binding at the N(7) position of a guanine base. Binding also occurs at the N(7) position of an adenine (A) base, but not as strongly. Coordination to two proximally disposed guanines (most common) or to a guanine or adenine (less common) base, respectively, affords Pt-GpG and Pt-ApG type inter- and intrastrand cross-links. It is postulated that the slower hydrolysis of the malonato (1,1,-cyclobutanedicarboxylic acid) leaving group in carboplatin, as compared with the highly labile chlorine ions in cisplatin, as well as it imparting increased aqueous solubility accounts for carboplatin's decreased toxicity. Intrastrand cross-linking is thought to be the critical lesion because it is believed that this type of bond causes only minor disruption to the DNA conformation. Minor changes are less likely to activate the DNA repair enzymes which have the DNA under constant surveillance. In contrast, interstrand, crossstrand and DNA-protein cross-links frequently activate repair enzymes which then remove the lesion. Resistance to further assault by agents of similar mechanism is rapidly acquired and thus, acquired resistance to cisplatin and similar drugs is encountered.

The correlation between the chemical structure of cisplatin analogs and their activities has been defined. Essentially, antitumor activity is best expressed when the platinum complex falls into the formula, cis-$A_2Pt^{II}X_2$ or cis-$A_2Pt^{IV}X_2Y_2$ structures. "A" is a cis-oriented organic amine ligand, preferably a primary amine or ammonia. A secondary amine is considerably less effective and a tertiary amine or non-hydrogen donating nitrogen will generally render the complex inactive. If $A_2$ represents a bidentate ligand (a ligand that is chelated to a metal ion by means of 2 donor atoms), it must be cis-coordinated and sterically nonobtrusive. "X" is required to be at least one easily exchangeable ligand such as chloride or a carboxylate group, and "Y" can represent two additional trans-oriented exchangeable polar groups such as RO⁻ or chloride. The active configuration of platinum is square planar and in the oxidation state of II. If introduced in the IV oxidation state the complex is cisplatin like inactive unless reduced in vivo to the II oxidation state by iron II or ascorbic acid, for example.

While the overall antitumor activity of cisplatin has not been significantly improved upon, replacing the chlorides with the less labile, but still exchangeable, malonato group, as in carboplatin, enhances aqueous solubility and considerably reduces dose-limiting nephrotoxicity and severe emetic properties.

In spite of many attempts, a single strategy that specifically addresses the crucial solubility, toxicity, and cell penetration problems has hitherto not been adequately addressed.

The approach utilized in the present invention involves targeting an agent for entry into the mitochondria Mitochondrial DNA (mtDNA) is considerably less complex than chromosomal DNA, yet it is a fully functional DNA that is equally vital to the cell. It is circular in structure and encodes for the two mitochondrial ribosome RNAs and 22 mitochondrial transfer RNAs that remain in the mitochondria to produce all 13 of the human proteins associated with mitochondrial function. Since the mitochondria modulate the energy requirements of a cell, tumor or otherwise, a disfunction in mtDNA replication would consequently kill the cell. In addition, mitochondria are intracellular components and, therefore, a method that targets an agent for entry into the mitochondria also potentially renders accessible other intracellular material such as chromosomal DNA in the process.

SUMMARY OF THE INVENTION

In accordance with the present invention, novel drug targeting agents are provided. Also provided is a method for treating neoplastic disorders using the agents of the present invention. Also provided are methods of treating diabetes, arthritic disorders and imaging using the agents of the present invention.

One embodiment of the present invention is an enantiopure agent having the structure:

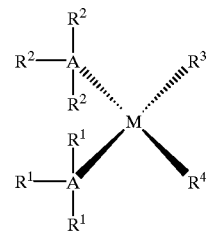

wherein each of $R^1$, $R^2$, $R^3$, $R^4$, $R_3^1A$ and $R_3^2A$ independently may be absent depending upon the metal's valence, provided that the desired pharmaceutical activity is maintained, and wherein each of A independently is N, O, P, S or a halide selected from the group chloro, fluoro, bromo and iodo, and wherein each of $R^1$ and $R^2$ independently is a lone pair of electrons or hydrogen or $R^5$, wherein $R^5$ is an unsaturated or saturated branched or unbranched aliphatic or alicyclic group having 1 to 50, preferably 1 to 8 and most preferably 1 to 5 carbon atoms, and optionally at least one hetero atom with the proviso that either $R^3$ or $R^4$ independently, or in combination are $R^6$ or at least one of $R^1$ or $R^2$ is $T^1$—$R^6$, or one of $R^1$ and one of $R^2$ in combination is

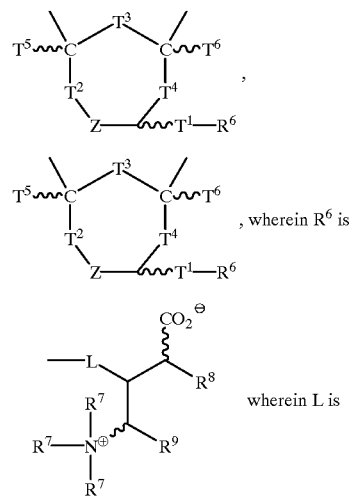

, wherein $R^6$ is wherein L is wherein $R^6$ is

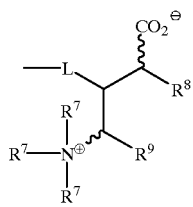

wherein L is O, S or $NR^{10}$, and wherein $R^7$ independently is hydrogen or an unsaturated or saturated branched or unbranched aliphatic or alicyclic group having from 1 to 6 carbon atoms, preferably 1 to 3 carbon atoms and most preferably 1 carbon atom, and optionally at least one hetero atom, wherein $R^{10}$ independently is hydrogen or an unsaturated or saturated branched or unbranched aliphatic or alicyclic group having from 1 to 6 carbon atoms, preferably 1 to 3 carbon atoms and most preferably 1 carbon atom, and optionally at least one hetero atom, wherein $R^8$ and $R^9$ independently is hydrogen or an unsaturated or saturated branched or unbranched aliphatic or alicyclic group having from one to 50 carbon atoms, preferably 5 to 25 carbon atoms, and most preferably 6 to 15 carbon atoms, and optionally at least one hetero atom, or $R^8$ and $R^9$ in combination is

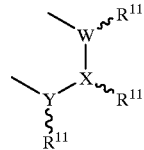

wherein each of W, X and Y independently is $(CR^{12})_p$, O, S, or N, wherein $R^{11}$ independently is a lone pair of electrons, $NR^{12}R^{13}$, $OR^{12}$, $SR^{12}$, or a hydrogen or an unsaturated or saturated branched or unbranched aliphatic or alicyclic group having from 1 to 50 carbon atoms, preferably 5 to 25 carbon atoms, and most preferably 6 to 15 carbon atoms, and optionally at least one hetero atom, wherein p is an integer of from 0–10, and preferably is 1, wherein each of $T^1$, $T^2$, $T^3$ and $T^4$ independently is an unsaturated branched or saturated branched or unbranched aliphatic or alicyclic group having 1 to 50, preferably 1 to 8 and most preferably 1 to 5 carbon atoms, and optionally includes at least one hetero atom, or is, or is in combination with, $(CR^{12}R^{13})_p$,

$C=NR^{13}$, $NR^{13}$, O, S, S=O, $SO_2$,

and wherein Z is $(CR^{12}R^{13})_n$,

$C=NR^{13}$, $NR^{13}$, O, S, S=O, $SO_2$ or a pair of terminating hydrogens, wherein each of $T^5$, $T^6$, $R^{12}$ and $R^{13}$ independently is hydrogen or an unsaturated or saturated branched or unbranched aliphatic or alicyclic group having from 1 to 50 carbon atoms, preferably 5 to 25 carbon atoms, and most preferably 6 to 15 carbon atoms, and wherein each of n and t independently is an integer of from 0 to 20, preferably 0 to 8, and most preferably 0 to 5, and wherein $R^3$ is $R^6$, $T^1$—$R^6$, $R_3^1A$, $OR^{14}$, $SR^{14}$ or a halide selected from the group consisting of chloro, fluoro, bromo, and iodo, wherein $R^4$ is $R^6$, $T^1$—$R^6$, $R_3^2A$, $OR^{15}$, $SR^{15}$ or a halide selected from the group consisting of chloro, fluoro, bromo, and iodo, wherein each of $R^{14}$ and $R^{15}$ independently is an unsaturated or saturated branched or unbranched aliphatic or alicyclic hetero or non hetero group having 1 to 50 carbon atoms, preferably 5 to 25 carbon atoms, and most preferably 6 to 15 carbons atoms and optionally at least one hetero atom, or $R^{14}$ and $R^{15}$ in combination is

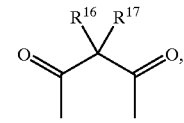

wherein each of $R^{16}$ and $R^{17}$ independently is hydrogen or an unsaturated or saturated branched or unbranched aliphatic or alicyclic group having 1 to 7 carbon atoms, preferably 1 to 5 carbon atoms, or $R^{16}$ and $R^{17}$ in combination is a cyclic aliphatic hetero or nonhetero group having 2 to 7 carbon atoms and optionally at least one hetero atom, and wherein M is selected from the group consisting of Pt, V, Mo, W, Mn, Tc, Fe, Ru, Co, Rh, Ni, Pd, Cu, Au, and Zn.

An additional embodiment of the present invention is a drug delivery system comprising an enantiopure agent having the structure:

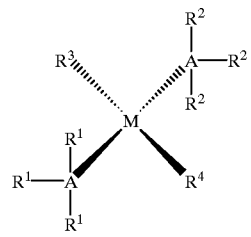

wherein each of $R^1$, $R^2$, $R^3$, $R^4$, $R_3^1A$ and $R_3^2A$ independently may be absent depending upon the metal's valence, provided that the desired pharmaceutical activity is maintained, and wherein each of A independently is N, O, P, S or a halide selected from the group chloro, fluoro, bromo and iodo, and wherein each of $R^1$ and $R^2$ independently is a lone pair of electrons or hydrogen or $R^5$, wherein $R^5$ is an unsaturated or saturated branched or unbranched aliphatic or alicyclic group having 1 to 50, preferably 1 to 8 and most preferably 1 to 5 carbon atoms, and optionally at least one hetero atom with the proviso that either each of $R^3$ or $R^4$ independently is $R^6$ or at least one of $R^1$ or $R^2$ is $T^1$—$R^6$, wherein $R^6$ is

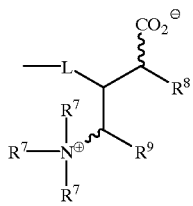

wherein L is O, S or NR$^{10}$, and wherein R$^7$ independently is hydrogen or an unsaturated or saturated branched or unbranched aliphatic or alicyclic group having from 1 to 6 carbon atoms, preferably 1 to 3 carbon atoms and most preferably 1 carbon atom, and optionally at least one hetero atom, wherein R$^{10}$ independently is hydrogen or an unsaturated or saturated branched or unbranched aliphatic or alicyclic group having from 1 to 6 carbon atoms, preferably 1 to 3 carbon atoms and most preferably 1 carbon atom, and optionally at least one hetero atom, wherein R$^8$ and R$^9$ independently is hydrogen or an unsaturated or saturated branched or unbranched aliphatic or alicyclic group having from one to 50 carbon atoms, preferably 5 to 25 carbon atoms, and most preferably 6 to 15 carbon atoms, and optionally at least one hetero atom, or R$^8$ and R$^9$ in combination is

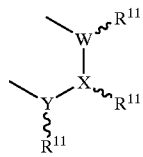

wherein each of W, X and Y independently is (CR$^{12}$)$_p$, O, S, or N, wherein R$^{11}$ independently is a lone pair of electrons, NR$^{12}$R$^{13}$, OR$^{12}$, SR$^{12}$, or a hydrogen or an unsaturated or saturated branched or unbranched aliphatic or alicyclic group having from 1 to 50 carbon atoms, preferably 5 to 25 carbon atoms, and most preferably 6 to 15 carbon atoms, and optionally at least one hetero atom, wherein p is an integer of from 0–10, and preferably is 1, wherein T$^1$, is an unsaturated branched or saturated branched or unbranched aliphatic or alicyclic group having 1 to 50, preferably 1 to 8 and most preferably 1 to 5 carbon atoms, and optionally includes at least one hetero atom, or is, or is in combination with, (CR$^{12}$R$^{13}$)$_p$,

C=NR$^{13}$, NR$^{13}$, O, S, S=O, SO$_2$,

and wherein each of R$^{12}$ and R$^{13}$ independently is hydrogen or an unsaturated or saturated branched or unbranched aliphatic or alicyclic group having from 1 to 50 carbon atoms, preferably 5 to 25 carbon atoms, and most preferably 6 to 15 carbon atoms, wherein t is an integer from 0 to 20, preferably 0 to 8 and most preferably 0 to 5, and wherein R$^3$ is R$^6$, T$^1$—R$^6$, R$_3^1$A, OR$^{14}$, SR$^{14}$ or a halide selected from the group consisting of chloro, fluoro, bromo, and iodo, wherein R$^4$ is R$^6$, T$^1$—R$^6$, R$_3^2$A, OR$^{15}$, SR$^{15}$ or a halide selected from the group consisting of chloro, fluoro, bromo, and iodo, wherein each of R$^{14}$ and R$^{15}$ independently is an unsaturated or saturated branched or unbranched aliphatic or alicyclic hetero or nonhetero group having 1 to 50 carbon atoms, preferably 5 to 25 carbon atoms, and most preferably 6 to 15 carbons atoms and optionally at least one hetero atom, or R$^{14}$ and R$^{15}$ in combination is

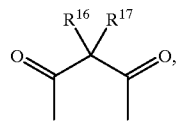

wherein each of R$^{16}$ and R$^{17}$ independently is hydrogen or an unsaturated or saturated branched or unbranched aliphatic or alicyclic group having 1 to 7 carbon atoms, preferably 1 to 5 carbon atoms, or R$^{16}$ and R$^{17}$ in combination is a cyclic aliphatic hetero or nonhetero group having 2 to 7 carbon atoms and optionally at least one hetero atom, and wherein M is selected from the group consisting of Pt, V, Mo, W, Mn, Tc, Fe, Ru, Co, Rh, Ni, Pd, Cu, Au, and Zn.

A further additional embodiment of the present invention is a drug delivery system comprising an enantiopure agent having the structure:

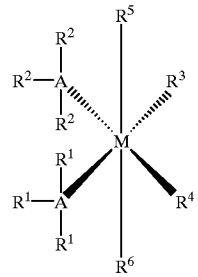

wherein each of R$^1$, R$^2$, R$^3$, R$^4$, R$^5$, R$^6$, R$_3^1$A and R$_3^2$A independently may be absent depending upon the metal's valence, provided that the desired pharmaceutical activity is maintained, and wherein each of A independently is N, O, P, S or a halide selected from the group chloro, fluoro, bromo and iodo, wherein each of R$^1$ and R$^2$ independently is a lone pair of electrons or hydrogen or R$^7$, wherein R$^7$ is an unsaturated or saturated branched or unbranched aliphatic or alicyclic group having 1 to 50, preferably 1 to 8 and most preferably 1 to 5 carbon atoms, and optionally at least one hetero atom with the proviso that either R$^3$, R$^4$, R$^5$ or R$^6$ independently or in combination are R$^8$ or at least one of R$^1$ or R$^2$ is T$^1$—R$^8$, or one of R$^1$ and one of R$^2$ in combination is

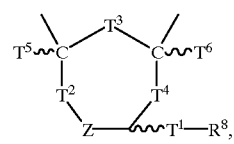

wherein $R^8$ is

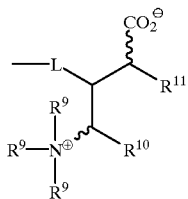

wherein L is O, S or $NR^{12}$, and wherein $R^9$ independently is hydrogen or an unsaturated or saturated branched or unbranched aliphatic or alicyclic group having from 1 to 6 carbon atoms, preferably 1 to 3 carbon atoms and most preferably 1 carbon atom, and optionally at least one hetero atom, wherein $R^{12}$ independently is hydrogen or an unsaturated or saturated branched CT unbranched aliphatic or alicyclic group having from 1 to 6 carbon atoms, preferably 1 to 3 carbon atoms and most preferably 1 carbon atom, and optionally at least one hetero atom, wherein $R^{10}$ and $R^{11}$ independently is hydrogen or an unsaturated or saturated branched or unbranched aliphatic or alicyclic group having from 1 to 50 carbon atoms, preferably 5 to 25 carbon atoms, and most preferably 6 to 15 carbon atoms, and optionally at least one hetero atom, or $R^{10}$ and $R^{11}$ in combination is

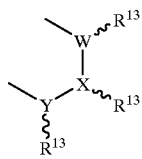

wherein each of X and Y independently is $(CR^{14})_p$, O, S, or N, wherein $R^{13}$ independently is a lone pair of electrons, $NR^{14}R^{15}$, $OR^{14}$, $SR^{14}$, or a hydrogen or an unsaturated or saturated branched or unbranched aliphatic or alicyclic group having from 1 to 50 carbon atoms, preferably 5 to 25 carbon atoms, and most preferably 6 to 15 carbon atoms, and optionally at least one hetero atom, wherein p is an integer of from 0–10, and preferably is 1, wherein each of $T^1$, $T^2$, $T^3$ and $T^4$ independently is an unsaturated branched or saturated branched or unbranched aliphatic or alicyclic group having 1 to 50, preferably 1 to 8 and most preferably 1 to 5 carbon atoms, and optionally includes at least one hetero atom, or is, or is in combination with, $(CR^{12}R^{13})_p$,

$C=NR^{13}$, $NR^{13}$, O, S, S=O, $SO_2$,

and wherein Z is $(CR^{14}R^{15})_n$,

$C=NR^{15}$, $NR^{15}$, O, S, S=O, $SO_2$ or a pair of terminating hydrogens, wherein each of $T^5$, $T^6$, $R^{14}$ and $R^{15}$ independently is hydrogen or an unsaturated or saturated branched or unbranched aliphatic or alicyclic group having from 1 to 50 carbon atoms, preferably 5 to 25 carbon atoms, and most preferably 6 to 15 carbon atoms, and optionally at least one hetero atom, and wherein each of n and t independently is an integer of from 0 to 20, preferably 0 to 8, and most preferably 0 to 5, and wherein $R^3$ is $R^8$, $T^1$—$R^8$, $R_3^1A$, $OR^{16}$, $SR^{16}$, or a halide selected from the group consisting of chloro, fluoro, bromo, and iodo, wherein $R^4$ is $R^8$, $T^1$—$R^8$, $R_3^2A$, $OR^{17}$, $SR^{17}$ or a halide selected from the group consisting of chloro, fluoro, bromo, and iodo, wherein $R^5$ is $R^8$, $T^1$—$R^8$, $R_3^1A$, $OR^{16}$, $SR^{16}$ or a halide selected from the group consisting of chloro, fluoro, bromo, and iodo, wherein $R^6$ is $R^8$, $T^1$—$R^8$, $R_3^2A$, $OR^{17}$, $SR^{17}$ or a halide selected from the group consisting of chloro, fluoro, bromo, and iodo, wherein each of $R^{16}$ and $R^{17}$ independently is an unsaturated or saturated branched or unbranched aliphatic or alicyclic hetero or nonhetero group having 1 to 50 carbon atoms, preferably 5 to 25 carbon atoms, and most preferably 6 to 15 carbons atoms and optionally at least one hetero atom, or $R^{16}$ and $R^{17}$ in combination is

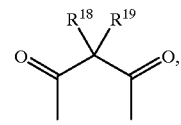

wherein each of $R^{18}$ and $R^{19}$ independently is hydrogen or an unsaturated or saturated branched or unbranched aliphatic or alicyclic group having 1 to 7 carbon atoms, preferably 1 to 5 carbon atoms, or $R^{18}$ and $R^{19}$ in combination is a cyclic aliphatic hetero or nonhetero group having 2 to 7 carbon atoms and optionally at least one hetero atom, and wherein M is selected from the group consisting of Pt, V, Mo, W, Mn, Tc, Fe, Ru, Co, Rh, Ni, Pd, Cu, Au, and Zn.

A further additional embodiment of the present invention is a drug delivery system comprising an enantiopure agent having the structure:

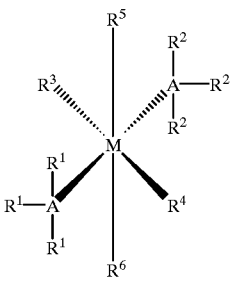

wherein each of $R^1$, $R^2$, $R^3$, $R^4$, $R^5$, $R^6$, $R_3^1A$ and $R_3^2A$ independently may be absent depending upon the metal's valence, provided that the desired pharmaceutical activity is maintained, and wherein each of A independently is N, O, P, S or a halide selected from the group chloro, fluoro, bromo and iodo, and wherein each of $R^1$ and $R^2$ independently is a lone pair of electrons or hydrogen or $R^7$, wherein $R^7$ is an unsaturated or saturated branched or unbranched aliphatic or alicyclic group having 1 to 50, preferably 1 to 8 and most preferably 1 to 5 carbon atoms, and optionally at least one hetero atom with the proviso that either $R^3$, $R^4$, $R^5$ or $R^6$ independently or in combination are $R^8$ or at least one of $R^1$ or $R^2$ is $T^1$—$R^8$, wherein $R^8$ is

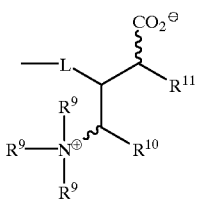

wherein L is O, S or $NR^{12}$, and wherein $R^9$ independently is hydrogen or an unsaturated or saturated branched or unbranched aliphatic or alicyclic group having from 1 to 6 carbon atoms, preferably 1 to 3 carbon atoms and most preferably 1 carbon atom, and optionally at least one hetero atom, wherein $R^{12}$ independently is hydrogen or an unsaturated or saturated branched or unbranched aliphatic or alicyclic group having from 1 to 6 carbon atoms, preferably 1 to 3 carbon atoms and most preferably 1 carbon atom, and optionally at least one hetero atom, wherein $R^{10}$ and $R^{11}$ independently is hydrogen or an unsaturated or saturated branched or unbranched aliphatic or alicyclic group having from 1 to 50 carbon atoms, preferably 5 to 25 carbon atoms, and most preferably 6 to 15 carbon atoms, and optionally at least one hetero atom, or $R^{10}$ and $R^{11}$ in combination is

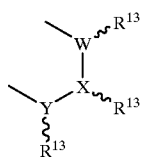

wherein each of W, X and Y independently is $(CR^{14})_p$, O, S, or N, wherein $R^{13}$ independently is a lone pair of electrons, $NR^{14}R^{15}$, $OR^{14}$, $SR^{14}$ or a hydrogen or an unsaturated or saturated branched or unbranched aliphatic or alicyclic group having from 1 to 50 carbon atoms, preferably 5 to 25 carbon atoms, and most preferably 6 to 15 carbon atoms, and optionally at least one hetero atom, wherein p is an integer of from 0–10, and preferably is 1, wherein $T^1$, is an unsaturated branched or saturated branched or unbranched aliphatic or alicyclic group having 1 to 50, preferably 1 to 8 and most preferably 1 to 5 carbon atoms, and optionally includes at least one hetero atom, or is, or is in combination with, $(CR^{12}R^{13})_t$,

$C=NR^{13}$, $NR^{13}$, O, S, S=O, $SO_2$,

and wherein each of $R^{14}$ and $R^{15}$ independently is hydrogen or an unsaturated or saturated branched or unbranched aliphatic or alicyclic group having from 1 to 50 carbon atoms, preferably 5 to 25 carbon atoms, wherein t is an integer from 0 to 20, preferably 0 to 8 and most preferably 0 to 5, and wherein $R^3$ is $R^8$, $T^1-R^8$, $R_3^1A$, $OR^{16}$, $SR^{16}$ or a halide selected from the group consisting of chloro, fluoro, bromo, and iodo, wherein $R^4$ is $R^8$, $T^1-R^8$, $R_3^2A$, $OR^{17}$, $SR^{17}$ or a halide selected from the group consisting of chloro, fluoro, bromo, and iodo, wherein $R^5$ is $R^8$, $T^1-R^8$, $R_3^1A$, $OR^{16}$, $SR^{16}$ or a halide selected from the group consisting of chloro, fluoro, bromo, and iodo, wherein $R^6$ is $R^8$, $T^1-R^8$, $R_3^2A$, $OR^{17}$, $SR^{17}$ or a halide selected from the group consisting of chloro, fluoro, bromo, and iodo, wherein each of $R^{16}$ and $R^{17}$ independently is an unsaturated or saturated branched or unbranched aliphatic or alicyclic hetero or nonhetero group having 1 to 50 carbon atoms, preferably 5 to 25 carbon atoms, and most preferably 6 to 15 carbons atoms and optionally at least one hetero atom, or $R^{16}$ and $R^{17}$ in combination is

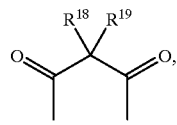

wherein each of $R^{18}$ and $R^{19}$ independently is hydrogen or an unsaturated or saturated branched or unbranched aliphatic or alicyclic group having 1 to 7 carbon atoms, preferably 1 to 5 carbon atoms, or $R^{18}$ and $R^{19}$ in combination is a cyclic aliphatic hetero or nonhetero group having 2 to 7 carbon atoms and optionally at least one hetero atom, and wherein M is selected from the group consisting of Pt, V, Mo, W, Mn, Tc, Fe, Ru, Co, Rh, Ni, Pd, Cu, Au, and Zn.

These and other advantages of the present invention will become apparent from the following detailed description.

DETAILED DESCRIPTION OF THE INVENTION

Figure 1:
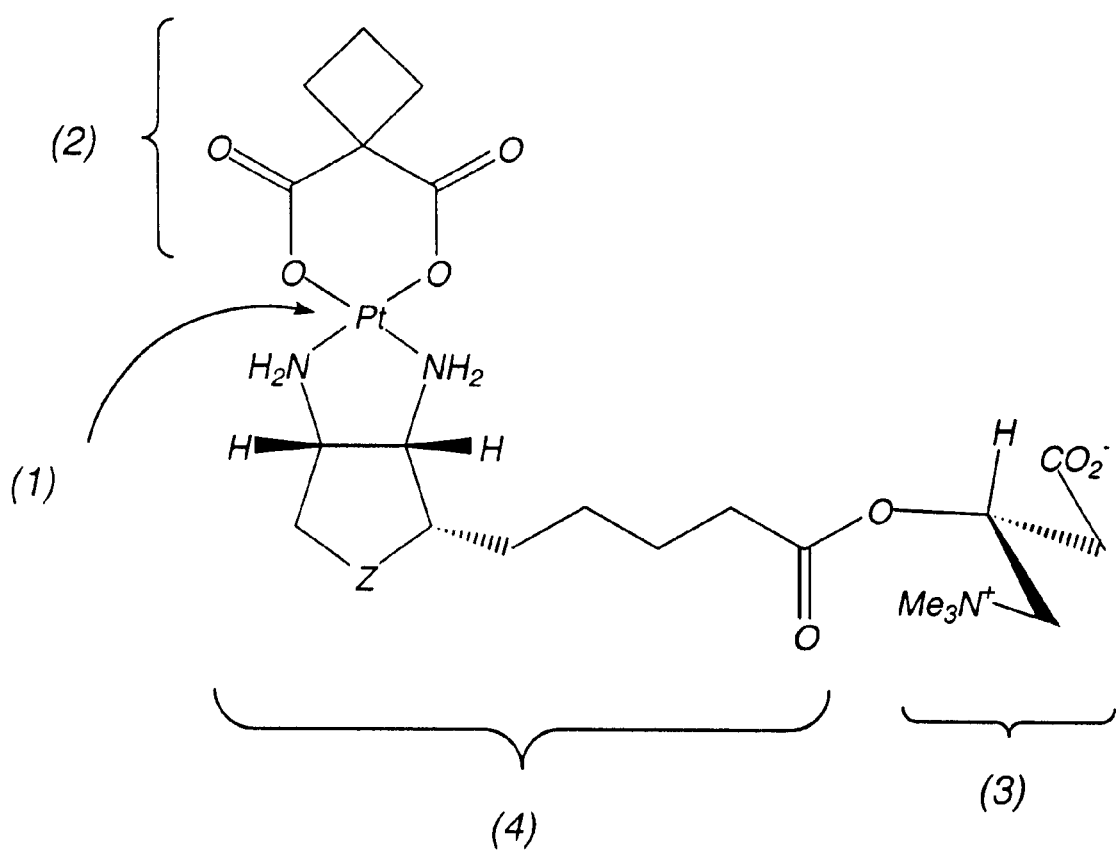
FIG. 1 depicts the structure of a mitoplatin.

Provided herein are novel targeted drug agents. Particularly, the novel agents of the present invention have a unique targetor which affords the agents access to the mitochondria via the acylcamitine translocase system. As used herein, the term targeted drug agent encompasses not only drugs as commonly understood, but also compounds useful in diagnostic applications. Also provided herein are methods of treating, diagnosing or monitoring diseases or conditions by using the novel targeted drug agents of the present invention. Preferably, the novel agents of the present invention are enantiopure. "Enantiopure" as used herein means a single geometrical isomer having optical activity.

The novel targeted drug agents of the present invention comprise a warhead unit, a triggering device, a targetor and optionally a carrier ligand. The warhead is a metal selected from the group consisting of, but not limited to, Pt, V, Mo, W, Mn, Tc, Fe, Ru, Co, Rh, Ni, Pd, Cu, Au and Zn. Other metal containing compounds having useful therapeutic or diagnostic utility may also be used. The triggering device is a group which releases the metal to the proper target location. Triggering devices include, but are not limited to, halides, malanoto, carboxylate, hetero atom substituted carboxylates, phosphates, sulfates, alkoxides, sulfides, selenides, phosphorous or nitrogen derivatives. The targetor is a compound which is susceptible to transport through the mitochondrial membrane via the L-carnitine acylcarnitine translocase system. These targetors include, but are not limited to, carnitine or carnitine analogs. Carnitine analogs include, but are not limited to (1S,2R,3R)-2-hydroxy-3-trimethylammoniocyclohexanecarboxylate, (1S,2R,3S)-2-hydroxy-3-trimethylammoniocyclohexanecarboxylate, (1R,2R,3R)-2-hydroxy-3-trimethylammoniocyclohexanecarboxylate, (1R,2R,3S)-2-hydroxy-3-trimethylammoniocyclohexanecarboxylate, D-3'-deoxy-3'-trimethylammonioglucuronate, and D-3'-deoxy-3'-trimethylammonioalluronate.

In some cases, it will be advantageous to use a carrier ligand. The carrier ligand couples the targetor to the warhead (metal). Suitable carrier ligands include, but are not limited to, γ-aminobutyric acid, 5-aminopentanoic acid, 6-aminocaproic acid, (4R)-4,5-diaminopentanoic acid, (4S)-4,5-diaminopentanoic acid, (5R)-5,6-diaminohexanoic acid, (5S)-5,6-diaminohexancic acid, (6R)-6,7-diaminoheptanoic acid, (6S)-6,7-diaminoheptanoic acid, (7R)-7,8-diaminooctanoic acid, (7S)-7,8-diaminooctanoic acid, 5-((1R,2R,3S)-2,3-diaminocyclopentyl)pentanoic acid, 5-((2S,3S,4R)-3,4-diaminothiacyclopentyl)pentanoic acid (from D-biotin), known also as descarbonylbiotin or (2S,3S,4R)-3,4-diaminotetrahydrothiophene-2-pentanoic acid, 5-((2S,3S,4R)-3,4-diamino-1-oxo-thiacyclopentyl)pentanoic acid, and 5-((2S,3S,4R)-3,4-diamino-1,1-dioxo-thiacyclopentyl)pentanoic acid, (7R,8S)-7,8-diaminononanoic acid (known also as 7,8-diaminopelargonic acid), (7S,8R)-7,8-diaminononanoic acid, and derivatives thereof.

One embodiment of the present invention is to provide novel targeted drug agents comprising platinum compounds. The term "platinum compounds" includes, but is not limited to, cisplatin, carboplatin or any of the numerous derivatives of the same.

The novel targeted drug agents of the present invention may be used to treat a variety of diseases and conditions, including, but not limited to, neoplastic disorders, immunological (i.e. AIDS, tissue rejection), neurodegenerative (i.e. dementia, Alzheimer's disease), skin, metabolic (i.e. diabetes), and arthritis disorders. In accordance with the present invention, compounds having antineoplastic (anticancer) effects are provided. Also provided is a method for treating neoplastic diseases using effective amounts of the agents of the present invention. The term "neoplastic" as used herein refers to progressive and indefinite multiplication of cells under conditions that would not elicit, or would cause, cessation of multiplication of normal cells. The novel drug agents of the present invention may also be used in diagnostic imaging, such as, but not limited to, tumor imaging, brain, lung, heart and bone scans. It is anticipated that the drug agents of the present invention will be most useful in treating or diagnosing diseases in which selected metalo-compounds have shown utility. For example, it is well known that certain platinum compounds, such as, but not limited to, cisplatin and carboplatin, are efficacious in treating cancer. It is also known that certain gold compounds are useful in treating arthritis and bullous skin disorders, and that certain vanadium compounds are useful as insulin mimetics. In diagnostic imaging, it is known that certain technicium or strontium compounds are useful in cardiovascular, bone, kidney and liver disease, infection and cancer, while gadolinium, iron and manganese for example have application in Magnetic Resonance Imaging (MRI) techniques. These are but a few examples of the types of metal containing compounds that can be used in the novel targeted drug agents of the present invention.

The drug agents of the present invention may be in the cis or in the trans configuration. Preferably, the drug agent is in the CIS configuration. In one embodiment of the present invention, the drug agent has the following structure:

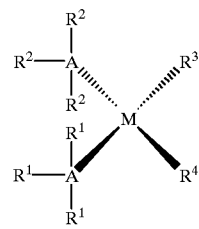

wherein each of $R^1$, $R^2$, $R^3$, $R^4$, $R_3{}^1A$ and $R_3{}^2A$ independently may be absent depending upon the metal's valence, provided that the desired pharmaceutical activity is maintained, and wherein each of A independently is N, O, P, S or a halide selected from the group chloro, fluoro, bromo and iodo, and wherein each of $R^1$ and $R^2$ independently is a lone pair of electrons or hydrogen or $R^5$, wherein $R^5$ is an unsaturated or saturated branched or unbranched aliphatic or alicyclic group having 1 to 50, preferably 1 to 8 and most preferably 1 to 5 carbon atoms, and optionally at least one hetero atom with the proviso that either $R^3$ or $R^4$ independently or in combination are $R^6$ or at least one of $R^1$ or $R^2$ is $T^1$—$R^6$, or one of $R^1$ and one of $R^2$ in combination is

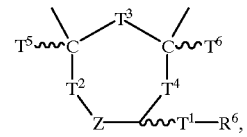

wherein $R^6$ is

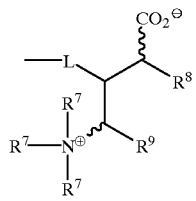

wherein L is O, S or $NR^{10}$, and wherein $R^7$ independently is hydrogen or an unsaturated or saturated branched or unbranched aliphatic or alicyclic group having from 1 to 6 carbon atoms, preferably 1 to 3 carbon atoms and most preferably 1 carbon atom, and optionally at least one hetero atom, wherein $R^{10}$ independently is hydrogen or an unsaturated or saturated branched or unbranched aliphatic or alicyclic group having from 1 to 6 carbon atoms, preferably 1 to 3 carbon atoms and most preferably 1 carbon atom, and optionally at least one hetero atom, wherein $R^8$ and $R^9$ independently is hydrogen or an unsaturated or saturated branched or unbranched aliphatic or alicyclic group having from one to 50 carbon atoms, preferably 5 to 25 carbon atoms, and most preferably 6 to 15 carbon atoms, and optionally at least one hetero atom, or $R^8$ and $R^9$ in combination is

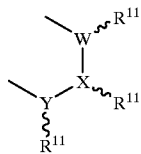

wherein each of W, X and Y independently is $(CR^{12})_p$, O, S, or N, wherein $R^{11}$ independently is a lone pair of electrons, $NR^{12}R^{13}$, $OR^{12}$, $SR^{12}$ or a hydrogen or an unsaturated or saturated branched or unbranched aliphatic or alicyclic group having from 1 to 50 carbon atoms, preferably 5 to 25 carbon atoms, and most preferably 6 to 15 carbon atoms, and optionally at least one hetero atom, wherein p is an integer of from 0–10, and preferably is 1, wherein each of $T^1$, $T^2$, $T^3$ and $T^4$ independently is an unsaturated branched or saturated branched or unbranched aliphatic or alicyclic group having 1 to 50, preferably 1 to 8 and most preferably 1 to 5 carbon atoms, and optionally includes at least one hetero atom, or is, or is in combination with, $(CR^{12}R^{13})_p$,

$C=NR^{13}$, $NR^{13}$, O, S, S=O, $SO_2$,

and wherein Z is $(CR^{12}R^{13})_n$,

$C=NR^{13}$, $NR^{13}$, O, S, S=O, $SO_2$ or a pair of terminating hydrogens, wherein each of $T^5$, $T^6$, $R^{12}$ and $R^{13}$ independently is hydrogen or an unsaturated or saturated branched or unbranched aliphatic or alicyclic group having from 1 to 50 carbon atoms, preferably 5 to 25 carbon atoms, and most preferably 6 to 15 carbon atoms, and wherein each of n and t independently is an integer of from 0 to 20, preferably 0 to 8, and most preferably 0 to 5, and wherein $R^3$ is $R^6$, $T^1$—$R^6$, $R_3^1A$, $OR^{14}$, $SR^{14}$ or a halide selected from the group consisting of chloro, fluoro, bromo, and iodo, wherein $R^4$ is $R^6$, $T^1$—$R^6$, $R_3^2A$, $OR^{15}$, $SR^{15}$ or a halide selected from the group consisting of chloro, fluoro, bromo, and iodo, wherein each of $R^{14}$ and $R^{15}$ independently is an unsaturated or saturated branched or unbranched aliphatic or alicyclic hetero or nonhetero group having 1 to 50 carbon atoms, preferably 5 to 25 carbon atoms, and most preferably 6 to 15 carbons atoms and optionally at least one hetero atom, or $R^{14}$ and $R^{15}$ in combination is

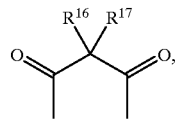

wherein each of $R^{16}$ and $R^{17}$ independently is hydrogen or an unsaturated or saturated branched or unbranched(1 aliphatic or alicyclic group having 1 to 7 carbon atoms, preferably 1 to 5 carbon atoms, or $R^{16}$ and $R^{17}$ in combination is a cyclic aliphatic hetero or nonhetero group having 2 to 7 carbon atoms and optionally at least one hetero atom, and wherein M is selected from the group consisting of Pt, V, Mo, W, Mn, Tc, Fe, Ru, Co, Rh, Ni, Pd, Cu, Au, and Zn.

An additional embodiment of the present invention is a drug delivery system comprising an enantiopure agent having the structure:

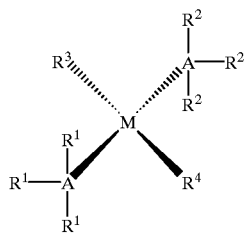

wherein each of $R^1$, $R^2$, $R^3$, $R^4$, $R_3^1A$ and $R_3^2A$ independently may be absent depending upon the metal's valence, provided that the desired pharmaceutical activity is maintained, and wherein each of A independently is N, O, P, S or a halide selected from the group chloro, fluoro, bromo and iodo, and wherein each of $R^1$ and $R^2$ independently is a lone pair of electrons or hydrogen or $R^5$, wherein $R^5$ is an unsaturated or saturated branched or unbranched aliphatic or alicyclic group having 1 to 50, preferably 1 to 8 and most preferably 1 to 5 carbon atoms, and optionally at least one hetero atom with the proviso that either each of $R^3$ or $R^4$ independently is $R^6$ or at least one of $R^1$ or $R^2$ is $T^1$—$R^6$, wherein $R^6$ is

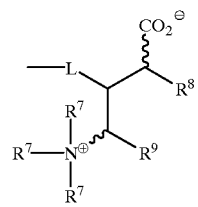

wherein L is O, S or $NR^{10}$, and wherein $R^7$ independently is hydrogen or an unsaturated or saturated branched or unbranched aliphatic or alicyclic group having from 1 to 6 carbon atoms, preferably 1 to 3 carbon atoms and most preferably 1 carbon atom, and optionally at least one hetero atom, wherein $R^{10}$ independently is hydrogen or an unsaturated or saturated branched or unbranched aliphatic or alicyclic group having from 1 to 6 carbon atoms, preferably 1 to 3 carbon atoms and most preferably 1 carbon atom, and optionally at least one hetero atom, wherein $R^8$ and $R^9$ independently is hydrogen or an unsaturated or saturated branched or unbranched aliphatic or alicyclic group having from one to 50 carbon atoms, preferably 5 to 25 carbon atoms, and most preferably 6 to 15 carbon atoms, and optionally at least one hetero atom, or $R^8$ and $R^9$ in combination is

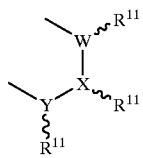

wherein each of W, X and Y independently is $(CR^{12})_p$, O, S, or N, wherein $R^{11}$ independently is a lone pair of electrons, $NR^{12}R^{13}$, $OR^{12}$, $SR^{12}$ or a hydrogen or an unsaturated or saturated branched or unbranched aliphatic or alicyclic group having from 1 to 50 carbon atoms, preferably 5 to 25 carbon atoms, and most preferably 6 to 15 carbon atoms, and optionally at least one hetero atom, wherein p is an integer of from 0–10, and preferably is 1, wherein $T^1$ is an unsaturated branched or saturated branched or unbranched aliphatic or alicyclic group having 1 to 50, preferably 1 to 8 and most preferably 1 to 5 carbon atoms, and optionally includes at least one hetero atom, or is, or is in combination with, $(CR^{12}R^{13})_t$,

$C=NR^{13}$, $NR^{13}$, O, S, S=O, $SO_2$,

and wherein each of $R^{12}$ and $R^{13}$ independently is hydrogen or an unsaturated or saturated branched or unbranched aliphatic or alicyclic group having from 1 to 50 carbon atoms, preferably 5 to 25 carbon atoms, and most preferably 6 to 15 carbon atoms, wherein t is an integer from 0 to 20, preferably 0 to 8 and most preferably 0 to 5, and wherein $R^3$ is $R^6$, $T^1$—$R^6$, $R_3^1A$, $OR^{14}$, $SR^{14}$ or a halide selected from the group consisting of chloro, fluoro, bromo, and iodo, wherein $R^4$ is $R^6$, $T^1$—$R^6$, $R_3^2A$ $OR^{15}$, $SR^{15}$ or a halide selected from the group consisting of chloro, fluoro, bromo, and iodo, wherein each of $R^{14}$ and $R^{15}$ independently is an unsaturated or saturated branched or unbranched aliphatic or alicyclic hetero or nonhetero group having 1 to 50 carbon atoms, preferably 5 to 25 carbon atoms, and most preferably 6 to 15 carbons atoms and optionally at least one hetero atom, or $R^{14}$ and $R^{15}$ in combination is

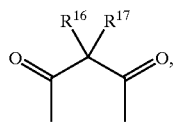

wherein each of $R^{16}$ and $R^{17}$ independently is hydrogen or an unsaturated or saturated branched or unbranched aliphatic or alicyclic group having 1 to 7 carbon atoms, preferably 1 to 5 carbon atoms, or $R^{16}$ and $R^{17}$ in combination is a cyclic aliphatic hetero or nonhetero group having 2 to 7 carbon atoms and optionally at least one hetero atom, and wherein M is selected from the group consisting of Pt, V, Mo, W, Mn, Tc, Fe, Ru, Co, Rh, Ni, Pd, Cu, Au, and Zn.

A further additional embodiment of the present invention is a drug delivery system comprising an enantiopure agent having the structure:

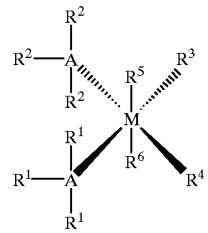

wherein each of $R^1$, $R^2$, $R^3$, $R^4$, $R^5$, $R^6$, $R_3^1A$ and $R_3^1A$ independently may be absent depending upon the metal's valence, provided that the desired pharmaceutical activity is maintained, and wherein each of A independently is N, O, P, S or a halide selected from the group chloro, fluoro, bromo and iodo, and wherein each of $R^1$ and $R^2$ independently is a lone pair of electrons or hydrogen or $R^7$, wherein $R^7$ is an unsaturated or saturated branched or unbranched aliphatic or alicyclic group having 1 to 50, preferably 1 to 8 and most preferably 1 to 5 carbon atoms, and optionally at least one hetero atom with the proviso that either $R^3$, $R^4$, $R^5$ or $R^6$ independently or in combination are $R^8$ or at least one of $R^1$ or $R^2$ is $T^1$—$R^8$, or one of $R^1$ and one of $R^2$ in combination is

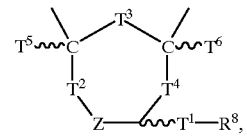

wherein $R^8$ is

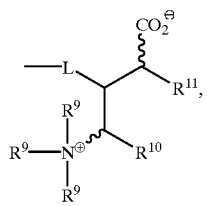

wherein L is O, S or $NR^{12}$, and wherein $R^9$ independently is hydrogen or an unsaturated or saturated branched or unbranched aliphatic or alicyclic group having from 1 to 6 carbon atoms, preferably 1 to 3 carbon atoms and most preferably 1 carbon atom, and optionally at least one hetero atom, wherein $R^{12}$ independently is hydrogen or an unsaturated or saturated branched or unbranched aliphatic or alicyclic group having from 1 to 6 carbon atoms, preferably 1 to 3 carbon atoms and most preferably 1 carbon atom, and optionally at least one hetero atom, wherein $R^{10}$ and $R^{11}$ independently is hydrogen or an unsaturated or saturated branched or unbranched aliphatic or alicyclic group having from 1 to 50 carbon atoms, preferably 5 to 25 carbon atoms, and most preferably 6 to 15 carbon atoms, and optionally at least one hetero atom, or $R^{10}$ and $R^{11}$ in combination is

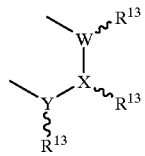

wherein each of W, X and Y independently is $(CR^{14})p$, O, S, or N, wherein $R^{13}$ independently is a lone pair of electrons, $NR^{14}R^{15}$, $OR^{14}$, $SR^{14}$ or a hydrogen or an unsaturated or saturated branched or unbranched aliphatic or alicyclic group having from 1 to 50 carbon atoms, preferably 5 to 25 carbon atoms, and most preferably 6 to 15 carbon atoms, and optionally at least one hetero atom, wherein p is an integer of from 0–10, and preferably is 1, wherein each of $T^1$, $T^2$, $T^3$ and T4 independently is an unsaturated branched or saturated branched or unbranched aliphatic or alicyclic group having 1 to 50, preferably 1 to 8 and most preferably 1 to 5 carbon atoms, and optionally includes at least one hetero atom, or is, or is in combination with, $(CR^{12}R^{13})_t$,

$C=NR^{13}$, $NR^{13}$, O, S, S=O, $SO_2$,

and wherein Z is $(CR^{14}R^{15})_n$,

$C=NR^{15}$, $NR^{15}$, O, S, S=O, $SO_2$ or a pair of terminating hydrogens, wherein each of $T^5$, $T^6$, $R^{14}$ and $R^{15}$ independently is hydrogen or an unsaturated or saturated branched or unbranched aliphatic or alicyclic group having from 1 to 50 carbon atoms, preferably 5 to 25 carbon atoms, and most preferably 6 to 15 carbon atoms, and optionally at least one hetero atom, and wherein each of n and t independently is an integer of from 0 to 20, preferably 0 to 8, and most preferably 0 to 5, and wherein $R^3$ is $R^8$, $T^1$—$R^8$, $R_3^1A$, $OR^{16}$, $SR^{16}$ or a halide selected from the group consisting of chloro, fluoro, bromo, and iodo, wherein $R^4$ is $R^8$, $T^1$—$R^8$, $R_3^2A$, $OR^{17}$, $SR^{17}$ or a halide selected from the group consisting of chloro, fluoro, bromo, and iodo, wherein $R^5$ is $R^8$, $T^1$—$R^8$, $R_3^1A$, $OR^{16}$, $SR^{16}$ or a halide selected from the group consisting of chloro, fluoro, bromo, and iodo, wherein $R^6$ is $R^8$, $T^1$—$R^8$, $R_3^2A$, $OR^{17}$, $SR^{17}$ or a halide selected from the group consisting of chloro, fluoro, bromo, and iodo, wherein each of $R^{16}$ and $R^{17}$ independently is an unsaturated or saturated branched or unbranched aliphatic or alicyclic hetero or nonhetero group having 1 to 50 carbon atoms, preferably 5 to 25 carbon atoms, and most preferably 6 to 15 carbons atoms and optionally at least one hetero atom, or $R^{16}$ and $R^{17}$ in combination is

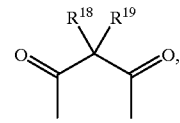

wherein each of $R^{18}$ and $R^{19}$ independently is hydrogen or an unsaturated or saturated branched or unbranched aliphatic or alicyclic group having 1 to 7 carbon atoms, preferably 1 to 5 carbon atoms, or $R^{18}$ and $R^{19}$ in combination is a cyclic aliphatic hetero or nonhetero group having 2 to 7 carbon atoms and optionally at least one hetero atom, and wherein M is selected from the group consisting of Pt, V, Mo, W, Mn, Tc, Fe, Ru, Co, Rh, Ni, Pd, Cu, Au, and Zn.

A further additional embodiment of the present invention is a drug delivery system comprising an enantiopure agent having the structure:

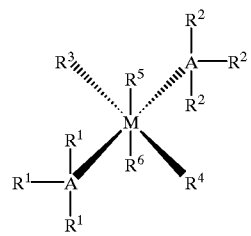

wherein each of $R^1$, $R^2$, $R^3$, $R^4$, A, $R^6$, $R_3^1A$ and $R_3^2A$ independently may be absent depending upon the metal's valence, provided that the desired pharmaceutical activity is maintained, and wherein each of A independently is N, O, P, S or a halide selected from the group chloro, fluoro, bromo and iodo, and wherein each of $R^1$ and $R^2$ independently is a lone pair of electrons or hydrogen or $R^7$, wherein $R^7$ is an unsaturated or saturated branched or unbranched aliphatic or alicyclic group having 1 to 50, preferably 1 to 8 and most preferably 1 to 5 carbon atoms, and optionally at least one hetero atom with the proviso that either $R^3$, $R^4$, $R^5$ or $R^6$ independently or in combination are $R^8$ or at least one of $R^1$ or $R^2$ is $T^1$—$R^8$, wherein $R^8$ is

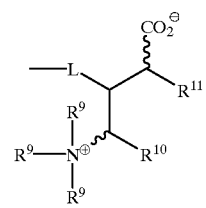

wherein L is O, S or $NR^{12}$, and wherein $R^9$ independently is hydrogen or an unsaturated or saturated branched or unbranched aliphatic or alicyclic group having from 1 to 6 carbon atoms, preferably 1 to 3 carbon atoms and most preferably 1 carbon atom, and optionally at least one hetero atom, wherein $R^{12}$ independently is hydrogen or an unsaturated or saturated branched or unbranched aliphatic or alicyclic group having from 1 to 6 carbon atoms, preferably 1 to 3 carbon atoms and most preferably 1 carbon atom, and optionally at least one hetero atom, wherein $R^{10}$ and $R^{11}$ independently is hydrogen or an unsaturated or saturated branched or unbranched aliphatic or alicyclic group having from 1 to 50 carbon atoms, preferably 5 to 25 carbon atoms, and most preferably 6 to 15 carbon atoms, and optionally at least one hetero atom, or $R^{10}$ and $R^{11}$ in combination is

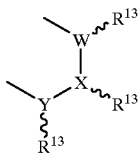

wherein each of W, X and Y independently is $(CR^{14})_p$, O, S, or N, wherein $R^{13}$ independently is a lone pair of electrons, $NR^{14}R^{15}$, $OR^{14}$, $SR^{14}$ or a hydrogen or an unsaturated or saturated branched or unbranched aliphatic or alicyclic group having from 1 to 50 carbon atoms, preferably 5 to 25 carbon atoms, and most preferably 6 to 15 carbon atoms, and optionally at least one hetero atom, wherein p is an integer of from 0–10, and preferably is 1, wherein $T^1$, is an unsaturated branched or saturated branched or unbranched aliphatic or alicyclic group having 1 to 50, preferably 1 to 8 and most preferably 1 to 5 carbon atoms, and optionally includes at least one hetero atom, or is, or is in combination with, $(CR^{12}R^{13})_t$,

$C{=}NR^{13}$, $NR^{13}$, O, S, S${=}$O, $SO_2$,

and wherein each of $R^{14}$ and $R^{15}$ independently is hydrogen or an unsaturated or saturated branched or unbranched aliphatic or alicyclic group having from 1 to 50 carbon atoms, preferably 5 to 25 carbon atoms, and most preferably 6 to 15 carbon atoms, wherein t is an integer from 0 to 20, preferably 0 to 8 and most preferably 0 to 5, and wherein $R^3$ is $R^8$, $T^1{-}R^8$, $R_3{}^1A$, $OR^6$, $SR^{16}$ or a halide selected from the group consisting of chloro, fluoro, bromo, and iodo, wherein $R^4$ is $R^8$, $T^1{-}R^8$, $R_3{}^2A$, $OR^{17}$, $SR^{17}$ or a halide selected from the group consisting of chloro, fluoro, bromo, and iodo, wherein $R^5$ is $R^8$, $T^1{-}R^8$, $R_3{}^1A$, $OR^{16}$, $SR^{16}$ or a halide selected from the group consisting of chloro, fluoro, bromo, and iodo, wherein $R^6$ is $R^8$, $T^1{-}R^8$, $R_3{}^2A$, $OR^{17}$, $SR^{17}$ or a halide selected from the group consisting of chloro, fluoro, bromo, and iodo, wherein each of $R^{16}$ and $R^{17}$ independently is an unsaturated or saturated branched or unbranched aliphatic or alicyclic hetero or nonhetero group having 1 to 50 carbon atoms, preferably 5 to 25 carbon atoms, and most preferably 6 to 15 carbons atoms and optionally at least one hetero atom, or $R^{16}$ and $R^{17}$ in combination is

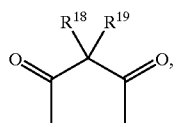

wherein each of $R^{18}$ and $R^{19}$ independently is hydrogen or an unsaturated or saturated branched or unbranched aliphatic or alicyclic group having 1 to 7 carbon atoms, preferably 1 to 5 carbon atoms, or $R^{18}$ and $R^{19}$ in combination is a cyclic aliphatic hetero or nonhetero group having 2 to 7 carbon atoms and optionally at least one hetero atom, and wherein M is selected from the group consisting of Pt, V, Mo, W, Mn, Tc, Fe, Ru, Co, Rh, Ni, Pd, Cu, Au, and Zn.

In a preferred embodiment of the present invention, the agent contains carnitine or a carnitine derivative such as, but not limited to aminocarnitine. In alternative embodiments, the agents of the invention contain carnitine derivatives that are not aminocarnitine.

In a preferred embodiment of the present invention, the metal is platinum and preferable structures are shown in FIG. 1. Compounds of this type are called mitoplatins—named because of their unique mitochondrial targeting ability and their platinum warhead. The mitoplatins also exhibit other desirable properties, one of which is high solubility. The extraordinary aqueous solubility of these compounds is a consequence of the zwitterionic character of the carnitine and carnitine derivatives such as, but not limited to, the carnitine-like esters. Solubility is of significant importance for drug delivery because it allows for both oral and intravenous routes to be considered for administering the agent. Furthermore, the high solubility permits the enhancement of the lipophilic nature of the mitoplatin. Lipophilicity is, known to be important for a wider spectrum of anti-tumor activity and reduced cross resistance with cisplatin. Perhaps the most significant advantage of the mitoplatins is that they exhibit minimal or no neurotoxicity against normal glial cells.

The mitoplatins were designed to include four specific functional elements. The platinum is, of course, the warhead (FIG. 1, 1) and is ultimately responsible for the anti neoplastic activity of the mitoplatins. The malonato group functions as a triggering device (2), releasing the platinum in the desired place. Although originally used to increase the water solubility of cisplatin, it is a milder leaving group than the original chloride ion. Thus, there art, fewer unproductive platinum complexes formed (e.g., platinum-protein complexes) with the less; active leaving group and DNA specificity is thereby increased. Of course, other triggering devices may be employed.

The unique functional feature of the mitoplatins is the targetor (3) which target, the molecule to the mitochondria via the L-carnitine acylcarnitine translocase system. The targetor may be L-carnitine or derivatives thereof. It is important to use the same natural stereochemistry (R) at the hydroxy bearing carbon in carnitine to avoid any potential antagonistic behavior with the natural function of carnitine and also to take advantage of the natural translocase pathway. This feature allows the targeting of neoplastic cells in tissues that: metabolize fatty acids such as the heart, muscle, liver, testes and epididymis. This includes neoplastic conditions such as, but not limited to breast, esophagus, lung, brain, prostate, kidney, liver, ovarian, testicular, cervical, pancreas, larynx, colon, thyroid, stomach, uterus, osteomatosis and melanoma.

In the example provided in FIG. 1, descarbonylbiotin functions as the carrier ligand (4) and couples the targetor to the rest of the molecule. Biotin is also known as vitamin H, and is an essential cofactor involved in carboxylation reactions, where it functions as a carrier of $CO_2$. Descarbonylbiotin and 7,8-diaminopelargonic acid are thought to be natural biosynthetic precursors to biotin and thus should not contribute to the toxicity of mitoplatins. The thioether group in descarbonylbiotin may cause some amount of polymerization during the chemical synthesis of the mitoplatins. However, this can be minimized by using the sulfoxide or sulphone derivatives of descarbonylbiotin or the desulfurized derivative, 7,8-diaminopelargonic acid, instead.

In alternative embodiments provided herein are drug targeting agents utilizing gold as the metal, M. Gold-containing compounds are useful in treating arthritic disorders and in treating dermatologic conditions such as, but not limited to, bullous skin disorders. Additionally, placement of vanadium as the metal provides useful insulin-mimetic agents. The novel targeting agents of the present invention may also be used in diagnostic applications.

The agents of the present invention may be administered orally, intravenously, intranasally, rectally or by any means which delivers an effective amount of the agent to the tissue or site to be treated. Suitable dosages are those which achieve the desired endpoint. It will be appreciated that different dosages may be required for treating different neoplastic disorders. An effective amount of an agent is that amount which causes a significant decrease in neoplastic cell count, growth, or size.

Those having ordinary skill in the art will be able to ascertain the most effective dose and times for administering the agents of the present invention, considering route of delivery, metabolism of the compound and other pharmacokinetic parameters such as volume of distribution, clearance, age of the subject, etc. The agents may be administered along with a pharmaceutical carrier and/or diluent.

The present invention is exemplified in terms of in vitro activity against various neoplastic cell lines. The test cell lines employed in the in vitro assays are well recognized and accepted as models for antitumor activity in animals. The term "animals" as used herein includes, but is not limited to, mice, rats, domesticated animals such as, but not limited to, cats and dogs, and other animals such as, but not limited to, cattle, sheep, pigs, horses, and primates such as, but not limited to, monkeys and humans.

The following examples serve to illustrate specific embodiments of the invention, but should not be considered as a limitation on the scope of the invention.

EXAMPLE 1

The following example demonstrates the synthesis of mitoplatins.

Figure 2:
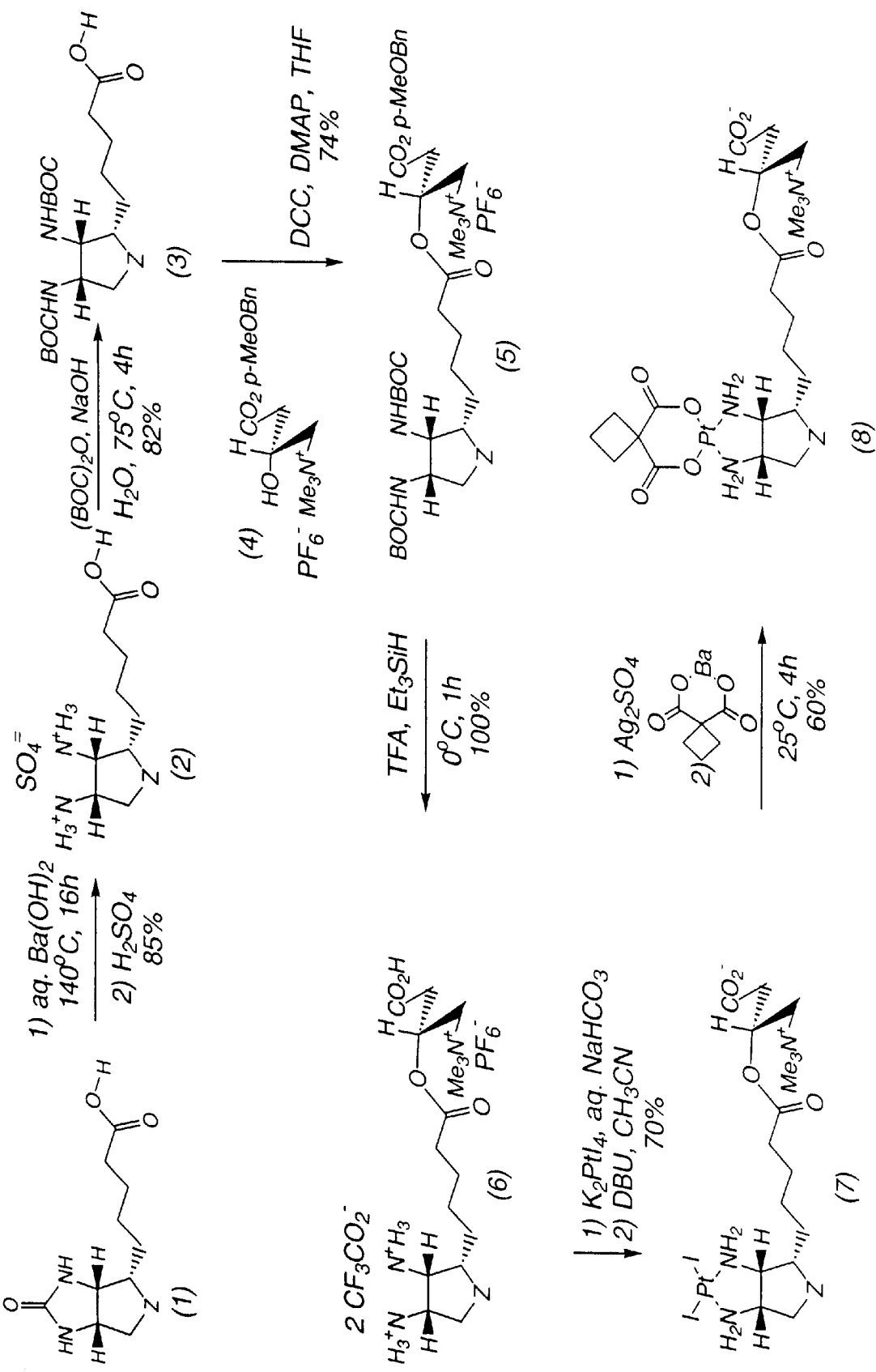
FIG. 2 depicts the synthesis of a mitoplatin.

The agents of the present invention are synthesized as shown in FIG. 2 and described as follows: D-(+) biotin (1) was converted into descarbonylbiotin sulphate (2) with aqueous Ba(OH)$_2$ at about 140° C. for about 16 hours. The barium salts were precipitated by acidification with sulfuric acid to give about 85% yield. The diamine was BOC (tert-butoxycarbonyl) protected to produce compound (3) in about 82% yield in NaOH, at about 75° C. for about 4 hours. Compound (3) was esterified with p-methoxybenzyl carnitine ester (compound 4) using a PF$_6^-$ counter ion to increase the organic solubility of the carnitine derivative and standard DCC coupling techniques (DCC/DMAP/THF), to produce compound (5) in about 74% yield. The protective groups were removed in a single step by treatment with. TFA/Et$_3$SiH, at about 0° C. for about 1 hour in about 100% yield. The resulting compound 6 was treated with K$_2$PtI$_4$ or K$_2$PtCl$_4$ (the figure depicts iodination) in aqueous NaHCO$_3$ and then with DBU (1,9-diazabicyclo[5.4.0]undec-7-ene) in acetonitrile to produce the diiodo- or dichloro-platinum (II) descarbonylbiotinylated carnitine ester derivative, compound (7) in about 70% yield. The synthesis was completed by in situ Ag$_2$SO$_4$ activation and the addition of stoichiometric amounts of barium, 1,1-cyclobutanedicarboxylate at 25° C. and stirring for about 4 hours to produce about 60% of the final product compound (8). The product was thereby produced in at least 22% overall yield and the precipitated salts were collected by filtration and lyophilization.

EXAMPLE 2

This example demonstrates the antitumor activity of the agents of the present invention.

The cytotoxicity of the mitoplatins was tested on an NIH 3T3 tumor cell line, and a human kidney fibroblast cell line. Cisplatin, carboplatin and the derivatives illustrated in FIG. 3 (KS-PT-5, KS-PT-6, KS-PT-7 and KS-PT-8) were tested according to the procedure of Alley et al., "Feasibility of Drug Screening with Panels of Human Tumor Cell Lines Using a Microculture Tetrazolium Assay", *Cancer Research*, 48:589–601 (1988) incorporated by, reference herein.

Figure 4A:
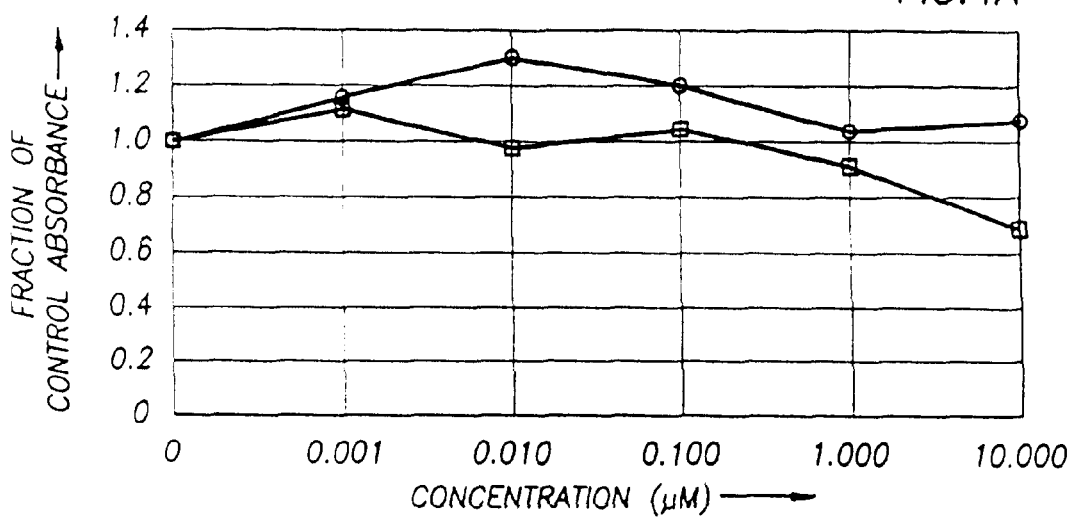
FIG. 4 depicts the results of NIH 3T3 cell line studies.
Figure 4B:
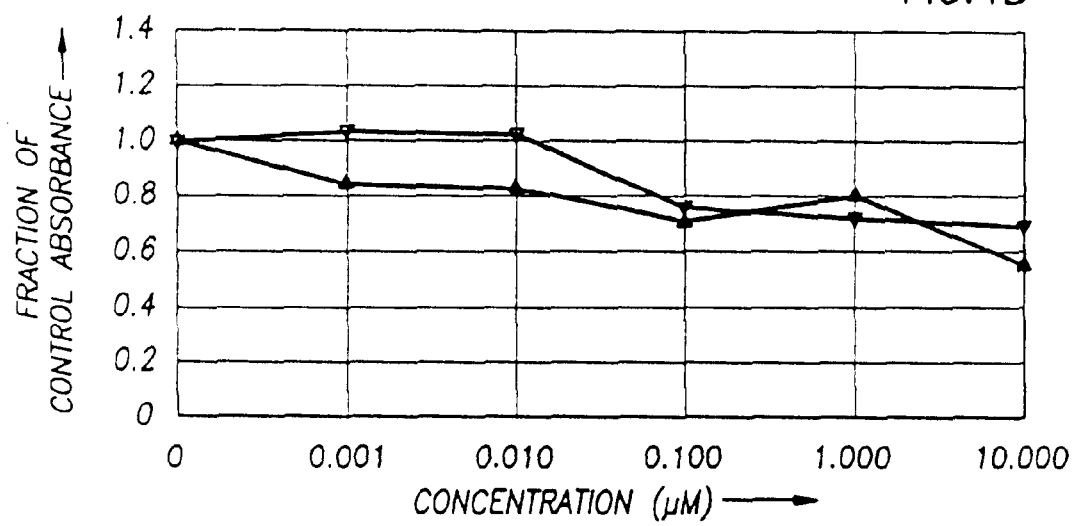
Figure 4C:
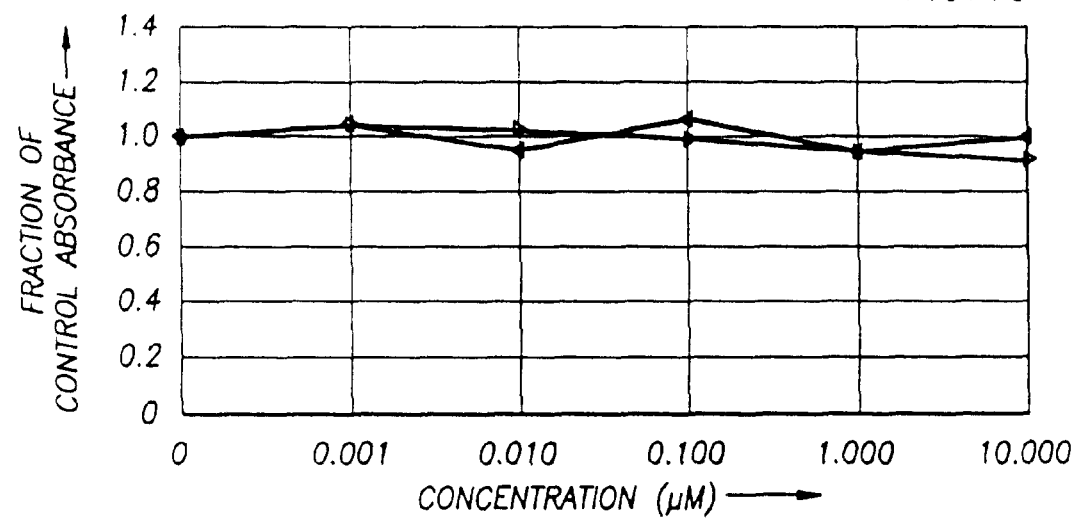
Figure 5A:
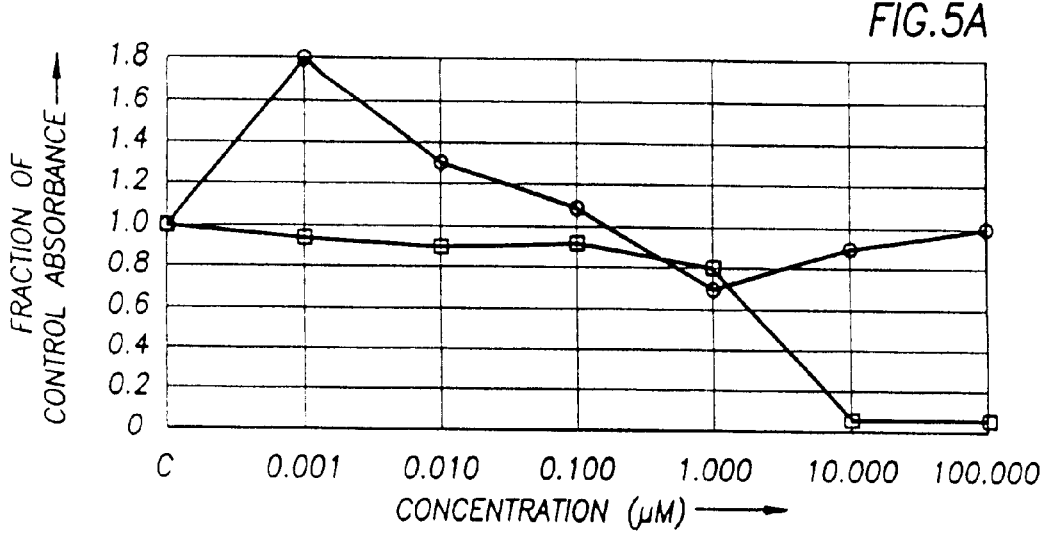
FIG. 5 depicts the results of studies with human kidney fibroblast cells.
Figure 5B:
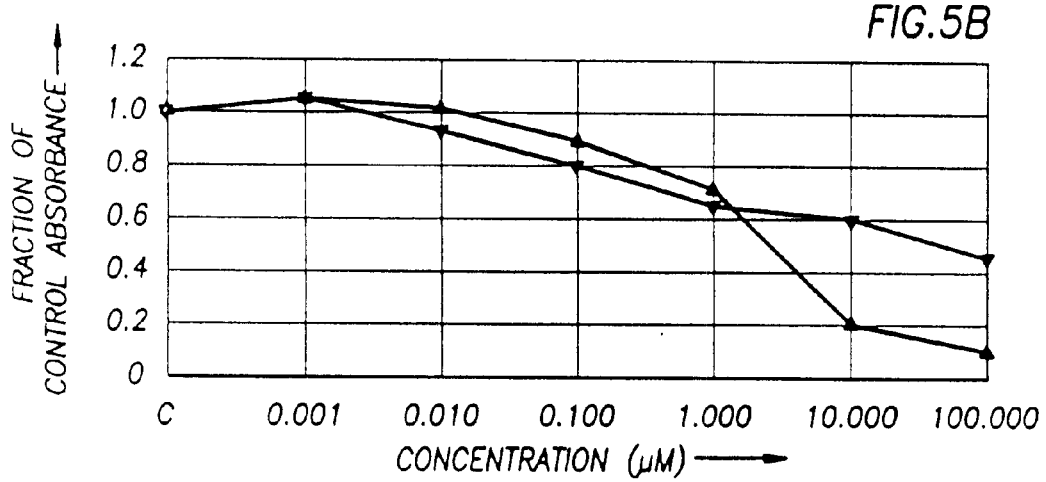
Figure 5C:
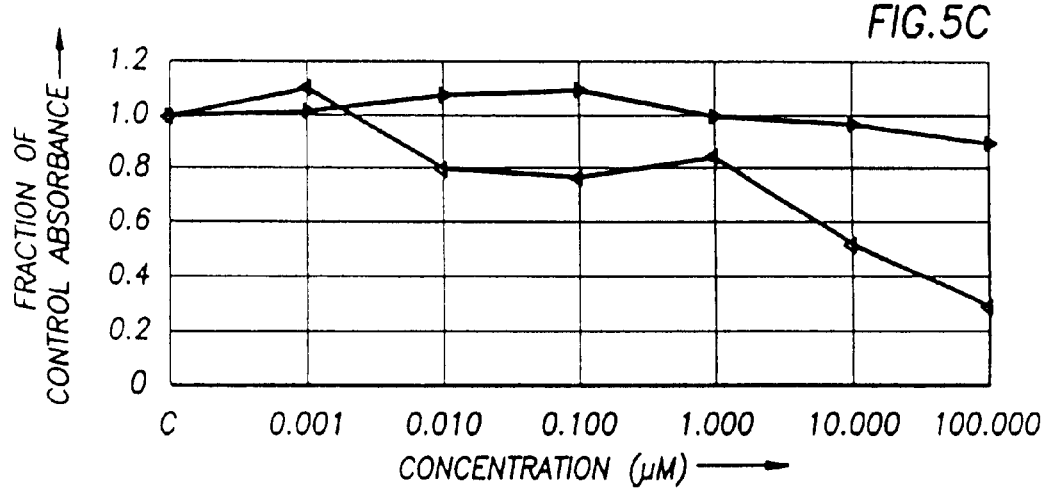

The results of the cytotoxicity test showed that agents having the carnitine substrate showed activity against the tumor cell lines. FIG. 4 depicts the results of the NIH 3T3 cell line studies. FIG. 4A shows cisplatin (open circles) and carboplatin (closed circles); 4B shows KS-PT-5 (open triangles) and KS-PT-6 (closed triangles); 4C shows KS-PT-7 (open squares) and KS-PT-8 (closed squares). FIG. 5 depicts the results in 293 human kidney fibroblast cells. 5A depicts cisplatin (open circles) and carboplatin (closed circles); 5B depicts KS-PT-5 (open circles) and KS-PT-6 (closed circles); 5C depicts KS-PT-7 (open circles) and KS-PT-8 (closed circles). FIGS. 4 and 5 are standard histograms depicting cell growth versus drug concentration. Compounds lacking the carnitine substrate KS-PT-7/8) showed no activity against the NIH 3T3 cell line and with 293 human kidney fibroblasts KS-Pt-8 has significant activity whereas KS-Pt-7 does not.

EXAMPLE 3

This example demonstrates the synthesis of carnitine analogs.

Figure 6:
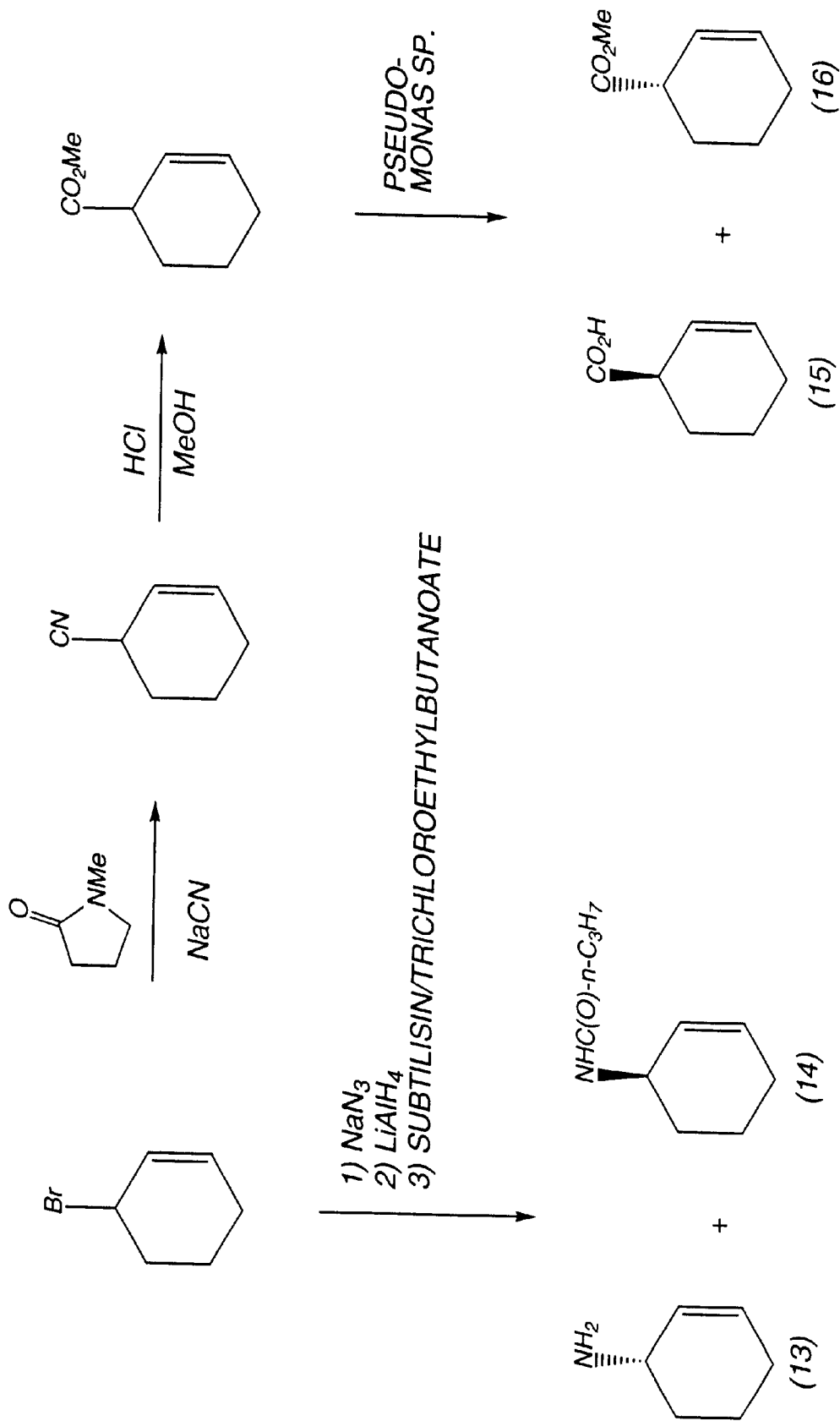
FIG. 6 illustrates the synthesis of carnitine analogs.
Figure 7:
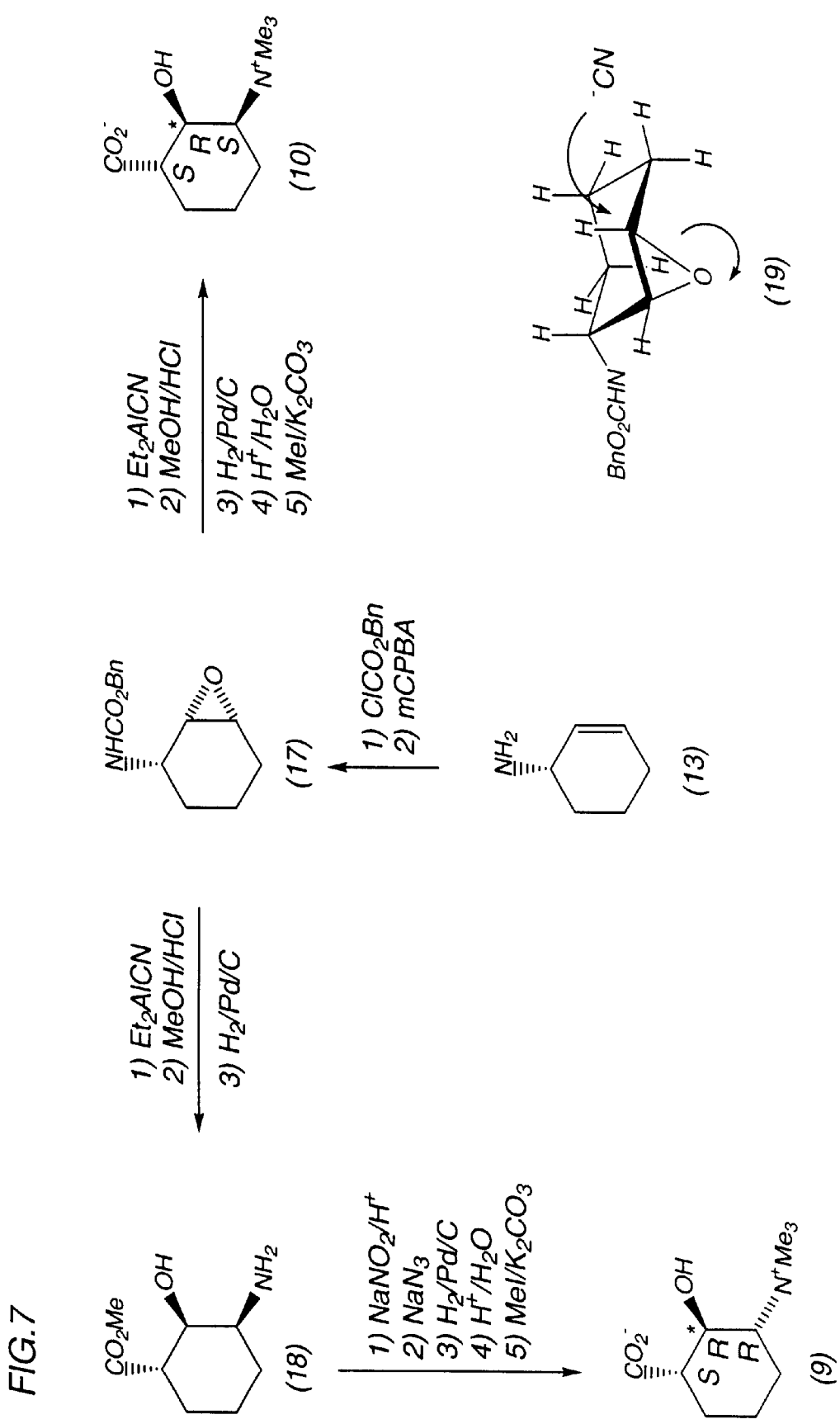
FIG. 7 illustrates the synthesis of carnitine analogs.
Figure 8:
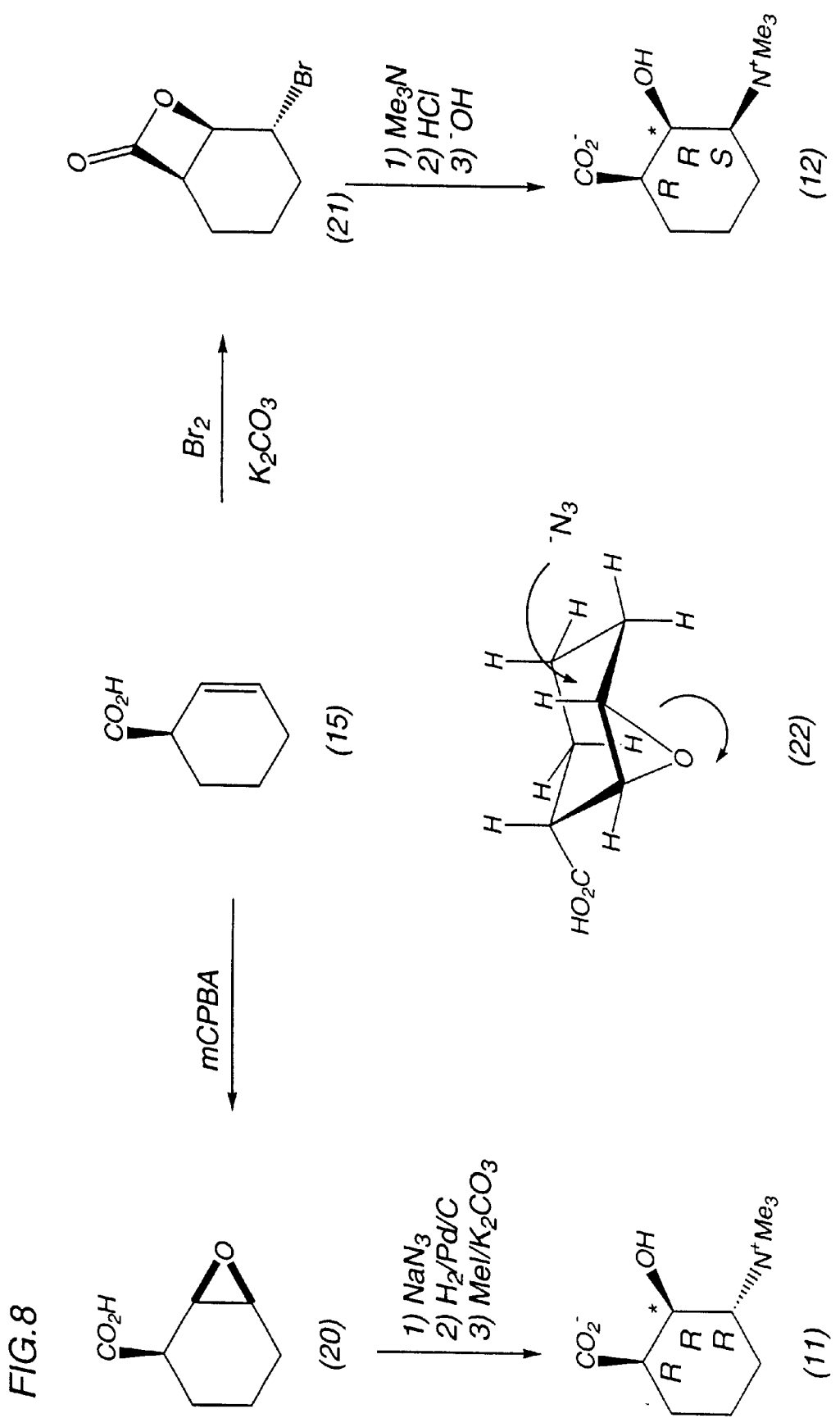
FIG. 8 illustrates the synthesis of carnitine analogs.

Preparation of enantiopure diastereomers, (1S,2R,3R)-2-hydroxy-3-trimethylammoniocyclohexanecarboxylate (9), (1S,2R,3S)-2-hydroxy-3-trimethylammoniocyclohexanecarboxylate (10), (1R,2R,3R)-2-hydroxy-3-trimethylammoniocyclohexanecarboxylate (11), and (1R,2R,3S)-2-hydroxy-3-trimethylammoniocyclohexanecarboxylate (12) from commercially available (±)-3-bromocyclohexene according to the schemes outlined in FIGS. 6, 7 and 8 is illustrative of the synthesis of carnitine analogs. The starred asymmetric carbon indicates identical stereochemistry with the hydroxy bearing carbon in L-carnitine.

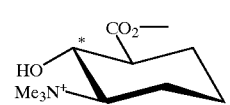

1S,2R,3R

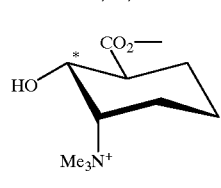

1S,2R,3R

-continued

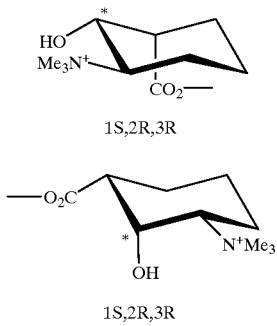

11

1S,2R,3R

12

1S,2R,3R

In FIG. 6, sodium azide displacement of the bromide in DMSO followed by lithium aluminum hydride reduction in diethyl ether and enzymatic resolution of the resulting allyl amine afforded after chromatographic separation enantiopure 13 and enantiopure 14. Whereas treatment (±)-3-bromocyclohexene with sodium cyanide afforded the corresponding nitrile which was converted into (±)-methyl-2-cyclohexenecarboxylate with dry HCl in methanol. Enzymatic resolution followed by chromatographic separation gave enantiopure 15 and enantiopure 16. In FIG. 7, relative stereochemical control of the three contiguous centers was achieved by protecting the amine functional group in 13 with benzylchloroformate and then carrying-out a diastereoselective syn-facial epoxidation of the double bond with m-chloroperoxybenzoic acid to obtain 17. Regioselective trans-diaxial opening of the epoxide with diethylaluminumcyanide (depicted by 19) followed by methanolysis and hydrogenolysis over Pd/C gave the free amino ester which was converted into enantiopure 10 by acid hydrolysis of the methyl ester and quaternization of the amine with methyl iodide and potassium carbonate in methanol. Alternatively, hydrogenolysis of the amino ester over Pd/C and conversion of the free amine into a diazonium salt was achieved with sodium nitrite in aqueous acetic acid. Azide displacement of the diazonium salt followed by reduction with hydrogen over Pd/C and then hydrolysis of the methyl ester and quaternization of the free amine with methyl iodide and potassium carbonate in methanol gave enantiopure 9.

In FIG. 8, enantiopure 2-cyclohexenecarboxylic acid 15 was syn-facially diastereoselectively epoxidized with m-chloroperoxybenzoic acid to obtain 20. Regioselective trans-diaxial opening of the epoxide with sodium azide (depicted by 22) followed by hydrogenolysis over Pd/C gave the free amino acid which was converted into enantiopure 11 by quaternization of the amine with methyl iodide and potassium carbonate in methanol. Bromolactonization of 15 afforded propiolactone 21 which was converted into enantiopure 12 by displacement of the bromide with trimethylamine, hydrolysis of the lactone with aqueous hydrochloric acid, and then neutralization with sodium hydroxide.

In each of the syntheses, the desired zwiterionic carnitine analog was separated from inorganic salts by eluting through a column of HP-20 or CHP-20p ion exchange resin. Further, the corresponding enantiopodes, (1R,2S,3S)-2-hydroxy-3-trimethylammoniocyclohexanecarboxylate (9e) and (1R,2S,3R)-2-hydroxy-3-trimethylammoniocyclohexanecarboxylate (10e), were independently prepared from 14. Hydrolysis of 14 into the free amine provided the enantiomer of 13 which when independently subjected to the same chemical reactions used for 9 and 10, gave enantiopure 9e and enantiopure 10e respectively. Whereas, (1S,2S,3S)-2-hydroxy-3trimethylammoniocyclohexanecarboxylate (11e) and (1S,2S,3R)-2-hydroxy-3trimethylammoniocyclohexanecarboxylate (12e) were prepared from 16. Saponification of 16 provided the enantiomer of 15 which when independently subjected to the same chemical reactions used for 11 and 12, gave enantiopure 11e and enantiopure 12e respectively.

Figure 9:
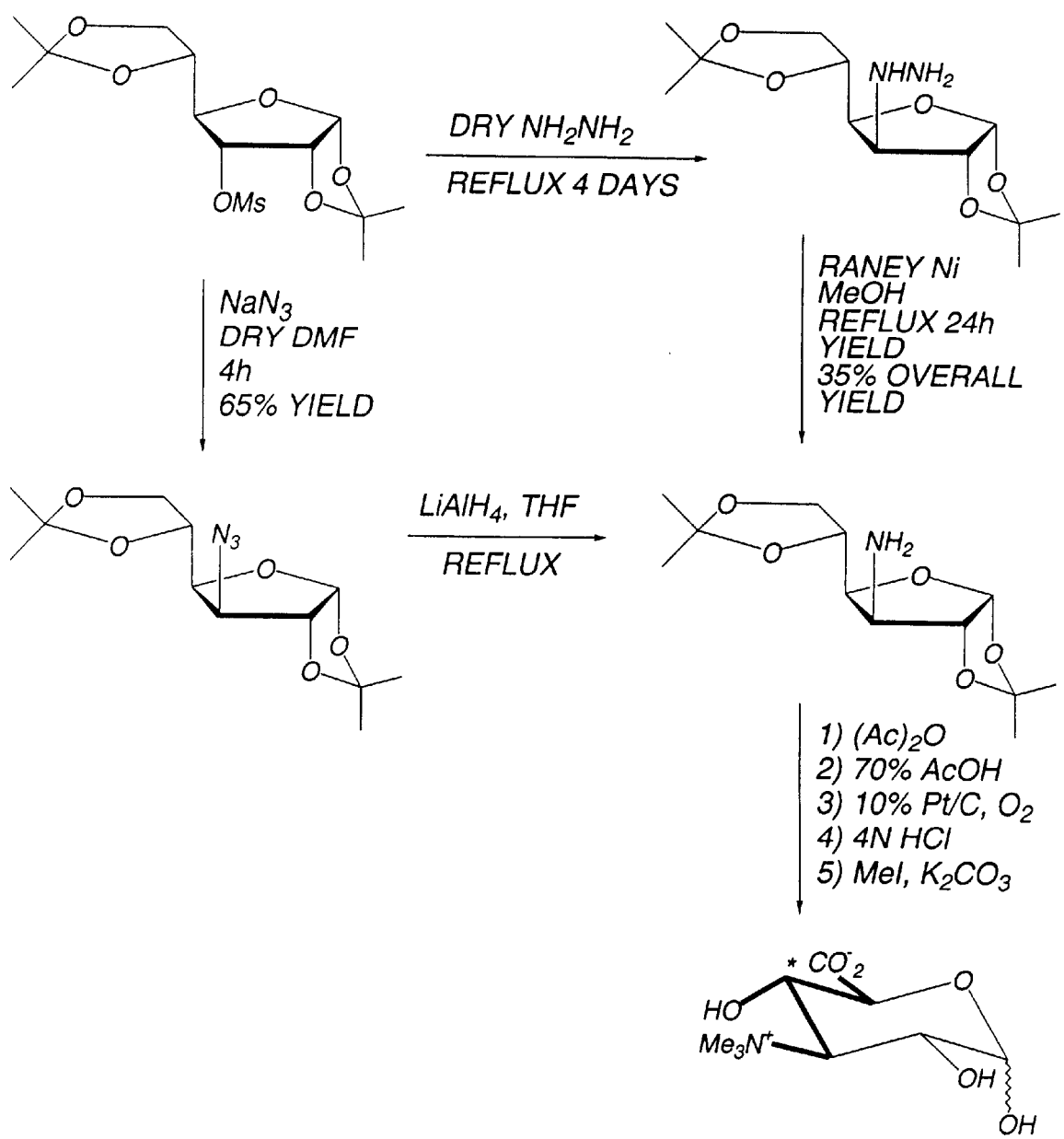
FIG. 9 depicts the preparation of an enantiopure polyfunctionalized carnitine.
Figure 10:
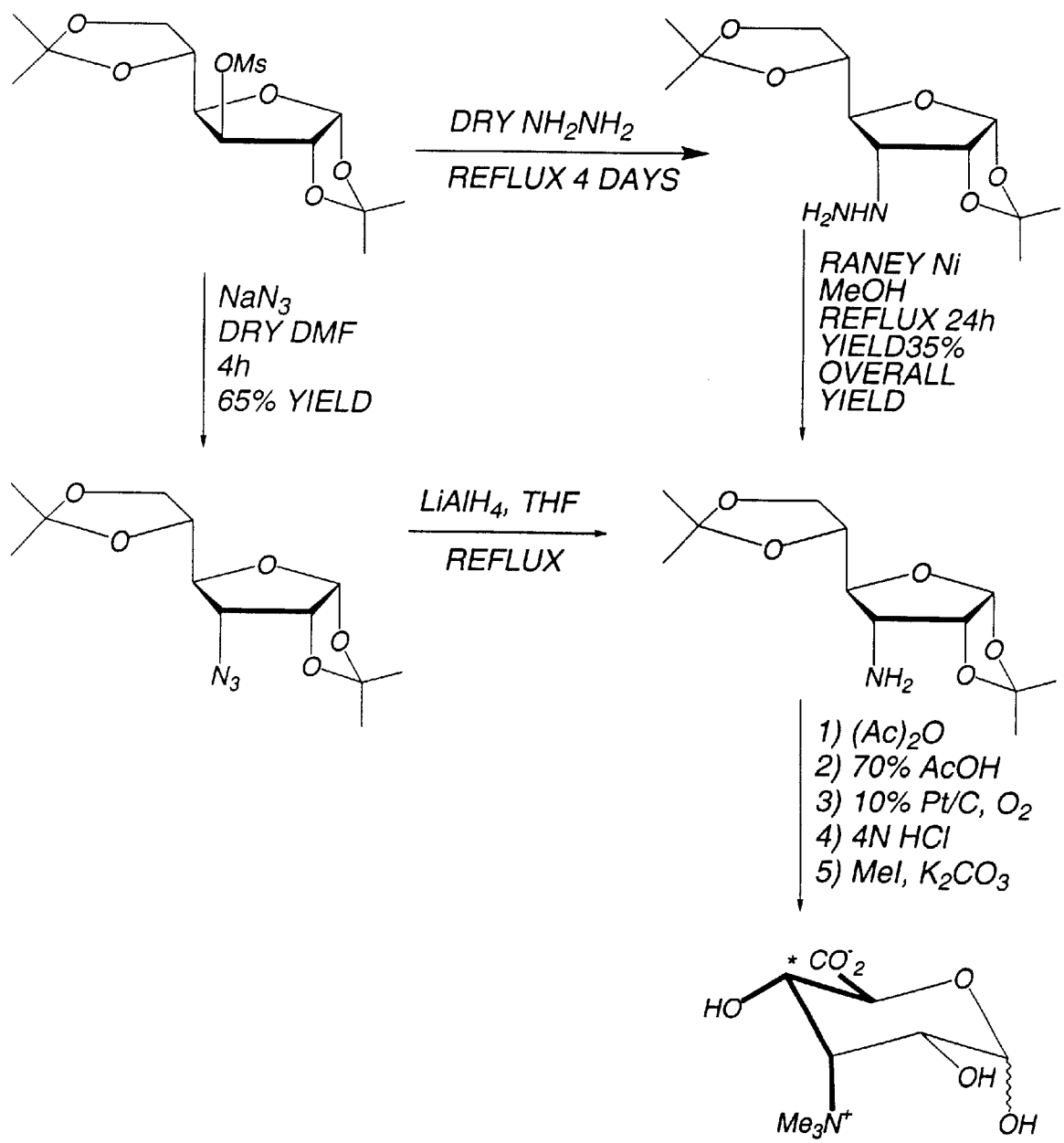
FIG. 10 depicts the preparation of an enantiopure polyfunctionalized carnitine.

An example of the preparation of an enantiopure polyfunctionalized carnitine analog is illustrated with the preparation of D-3'-deoxy-3'-trimethylammonioglucuronate (α and β-hydroxy anomers), having the following structural formula:

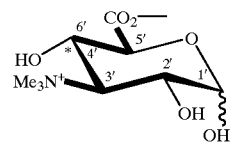

and with D-3'-deoxy-3'-trimethylammonioalluronate (α and β-hydroxy anomers), having the following structural formula:

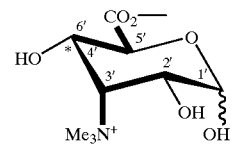

from commercially available 1,2:5,6-di-O-isopropylidene-3-O-(methylsulfonyl)-α-D-allofuranose using the chemical transformations depicted in FIG. 9 and from commercially available 1,2:5,6-di-O-isopropylidene-3-O-(methylsulfonyl)-α-D-glucofuranose using the chemical transformations depicted in FIG. 10, respectively.

EXAMPLE 4

This example demonstrates the DNA cross-linking studies using pTZSV28 DNA.

Figure 3:
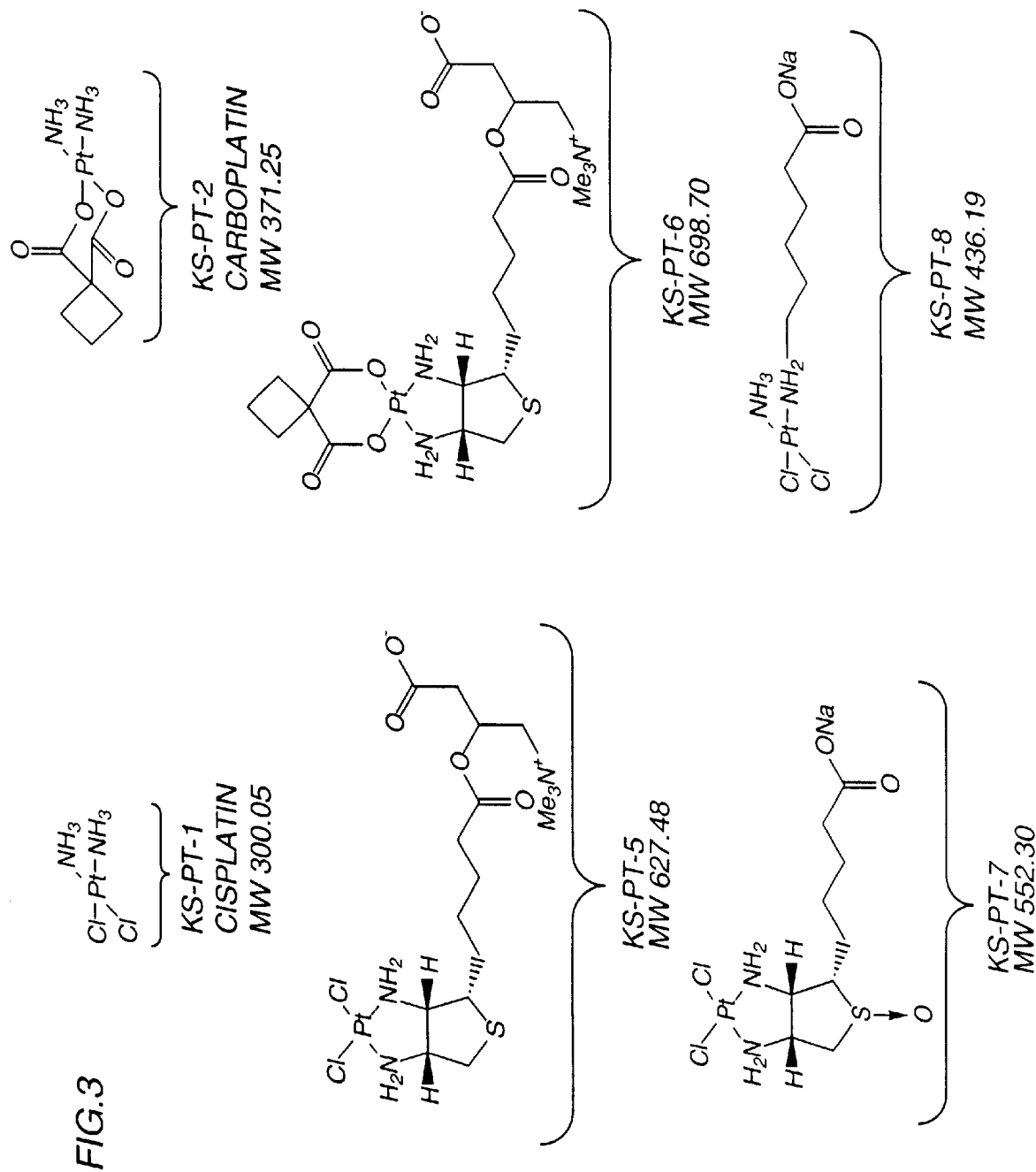
FIG. 3 depicts the structure of compounds tested.
Figure 11:
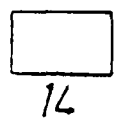
FIG. 11 depicts an autorad scan in a cross-linking assay.
Figure 11:
Figure 11:
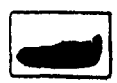
Figure 11:
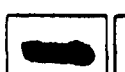
Figure 11:
Figure 11:
Figure 11:
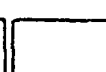
Figure 11:
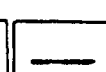
Figure 11:
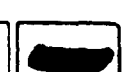
Figure 11:
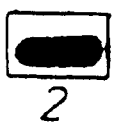
Figure 11:
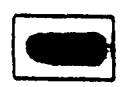
Figure 11:
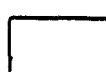
Figure 11:
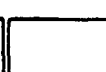
Figure 11:
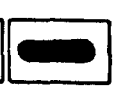
Figure 11:
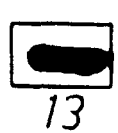
Figure 11:
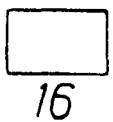
Figure 11:
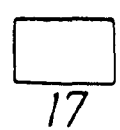

The DNA cross-linking of cisplatin, carboplatin and the derivatives illustrated in FIG. 3 (KS-Pt-5, KS-Pt-6, KS-Pt-7 and KS-Pt-8) were tested according to Hartley et al., "An Agarose Gel Method for the Determination of DNA Interstrand Crosslinking Applicable to the Measurement of the Rate of Total and "Second-Arm" Crosslink Reactions", Analytical Biochemistry, 193:131–134 (1991); and Loechler et al., "Construction of a Human Shuttle Vector Containing a Single Nitrogen Mustard Interstrand, DNA-DNA Cross-Link at a Unique Plasmid Location", Cancer Research, 51:2268–2772 (1991). FIG. 11 is a densitometer scan of the DNA (pTZSV28) cross-linking assay autorad with cisplatin (box 3), carboplatin (boxes 4 and 5), KS-Pt-5 (lane empty), KS-Pt-6 (boxes 6 and 7), KS-Pt-7 (boxes 8 and 9), KS-Pt-8 (boxes 10 and 11). Boxes 1 and 12 are double-strand DNA controls. Boxes 2 and 13 are denatured single-strand DNA controls. Boxes 14, 15, 16 and 17 are background readings. Table 1 shows the volume measurements off of the densitometer scan of the DNA (pTZSV28) cross-linking assay autorad with cisplatin, carboplatin, KS-Pt-5, KS-Pt-6, KS-Pt-7 and KS-Pt-8.

TABLE 1

| Box No. | Volume | % | Bg. Type | Average | Std. | Area |
|---|---|---|---|---|---|---|
| 1. | 2818.08 | 11.38 | LocalAvg | 0.489 | 0.211 | 17376 |
| 2. | 4598.94 | 18.58 | LocalAvg | 0.580 | 0.316 | 17376 |
| 3. | 1793.18 | 7.24 | LocalAvg | 0.388 | 0.127 | 17376 |
| 4. | 109.57 | 0.44 | LocalAvg | 0.284 | 0.018 | 17376 |
| 5. | 4853.68 | 19.61 | LocalAvg | 0.575 | 0.340 | 17376 |
| 6. | 206.18 | 0.83 | LocalAvg | 0.288 | 0.016 | 17376 |
| 7. | 11.75 | 0.05 | LocalAvg | 0.277 | 0.012 | 17376 |
| 8. | 349.90 | 1.41 | LocalAvg | 0.298 | 0.025 | 17376 |
| 9. | 465.35 | 1.88 | LocalAvg | 0.305 | 0.029 | 17376 |
| 10. | 375.06 | 1.52 | LocalAvg | 0.304 | 0.038 | 17376 |
| 11. | 2304.91 | 9.31 | LocalAvg | 0.417 | 0.166 | 17376 |
| 12. | 3317.52 | 13.40 | LocalAvg | 0.493 | 0.265 | 17376 |
| 13. | 3421.08 | 13.82 | LocalAvg | 0.505 | 0.233 | 17376 |
| 14. | 28.55 | 0.12 | LocalAvg | 0.275 | 0.011 | 17376 |
| 15. | −6.79 | NA | LocalAvg | 0.274 | 0.011 | 17376 |
| 16. | 98.89 | 0.40 | LocalAvg | 0.276 | 0.015 | 17376 |
| 17. | −20.31 | NA | LocalAvg | 0.275 | 0.013 | 17376 |

Cisplatin showed 100% of the area of the double stranded DNA control, and carboplatin ~100% of the area of the single stranded DNA control. KS-Pt-5 showed 100% DNA cleaving, and KS-Pt-6 had ~98% DNA cleaving with 2% of the remaining DNA being a ~95% double-stranded and ~5% single-stranded. KS-Pt-7 had ~82% DNA cleaving with the remaining 18% DNA being ~43% double-stranded and 57% single-stranded, and KS-Pt-8 had ~52% DNA cleaving with the remaining 48% being about 14% double-stranded and about 86% single-stranded DNA cleaving. These studies demonstrate that KS-Pt-5 and KS-Pt-6 essentially show no cross-linking. This observation is important since cross-linking causes the DNA repair process to kick in. When carnitine is absent (KS-Pt-7), there is less DNA cleaving and what remains is essentially equally double-stranded and single-stranded.

Many other variations and modifications may be made in the methods herein, described, by those having experience in this art, without departing from the concept of the, present invention. Accordingly, it should be clearly understood that the methods described in. the foregoing description are illustrative only and not intended as a limitation on the scope of the invention.

What is claimed is:

1. An enantiopure targeted agent, comprising:
    a targetor having the structure

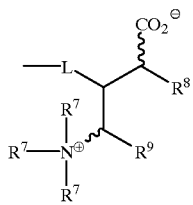

wherein L is O, S or $NR^{10}$, and wherein each R' independently is hydrogen or an unsaturated or saturated branched or unbranched aliphatic or alicyclic group having from 1 to 6 carbon atoms, and optionally at least one hetero atom, wherein $R^{10}$ is hydrogen or an unsaturated or saturated branched or unbranched aliphatic or alicyclic group having from 1 to 6 carbon atoms and optionally at least one hetero atom, wherein each of $R^3$ independently is hydrogen or unsaturated or saturated branched or unbranched aliphatic or alicyclic group having from one to 50 carbon atoms, and optionally at least one hetero atom, or $R^8$ and $R^9$ in combination is

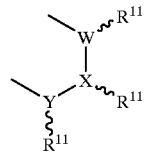

wherein each of W, X and Y independently is $(CR^{12})_p$, O, S or N, wherein each $R^{11}$ independently is a lone pair of electrons, $NR^{12}R^{13}$, $OR^{12}$, $SR^{12}$ or a hydrogen or an unsaturated or saturated branched or unbranched aliphatic or alicyclic group having from 1 to 50 carbon atoms, and optionally at least one hetero atom, wherein p is an integer of from 0 to 2, wherein each $R^{12}$ and $R^{13}$ independently is hydrogen or an unsaturated or saturated branched or unbranched aliphatic or alicyclic group having from 1 to 50 carbon atoms; and a metal containing pharmaceutical agent covalently bonded to the targetor.

2. The enantiopure targeted drug agent of claim 1, wherein the metal is selected from the group consisting of Pt, V, Mo, W, Mn, Tc, Fe, Ru, Co, Rh, Ni, Pd, Cu, Au, and Zn.

3. The enantiopure targeted drug agent according to claim 1 or 2, wherein the metal containing pharmaceutical agent is selected from the group consisting of cisplatin, carboplatin, and analogs thereof.

4. The enantiopure targeted drug agent according to claim 1, 2 or 3 further comprising the covalently bonded structure:

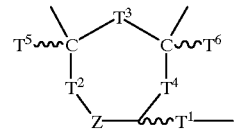

wherein each of $T^1$, $T^2$, $T^3$ and $T^4$ independently is an unsaturated branched or saturated branched or unbranched aliphatic or alicyclic group having 1 to 50 carbon atoms, and optionally includes at least one hetero atom, or is, in combination with, $(CR^{12}R^{13})_p$, $$\overset{O}{\underset{C,}{\|}}$$

$C=NR^{13}$, $NR^{13}$, O, S, S=O, $SO_2$, $$\overset{S}{\underset{C,}{\|}}$$

and wherein Z is $(CR^{12}CR^{13})_n$,

$C=NR^{12}$, $NR^{13}$, O, S, S=O, $SO_2$, or a pair of terminating hydrogens,
wherein each of $T^5$, $T^6$, $R^{12}$ and $R^{13}$ independently is hydrogen or an unsaturated or saturated branched or unbranched aliphatic or alicyclic group having from 1 to 50 carbon atoms, and optionally at least one hetero atom, and wherein each of n and t independently is an integer of from 0 to 20.

5. An enantiopure targeted drug agent having the structure:

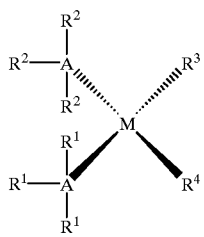

wherein each A independently is N, O, P, S or a halide selected from the group chloro, fluoro, bromo, iodo, and wherein each of $R^1$ and $R^2$ independently is a lone pair of electrons or hydrogen of $R^5$, wherein $R^5$ is an unsaturated or saturated branched or unbranched aliphatic or alicyclic group having 1 to 50 carbon atoms, and optionally at least one hetero atom with the proviso that either $R^3$ or $R^4$ independently or in combination with $R^6$ or at least one of $R^1$ or $R^2$ is $T^1$—$R^6$, or one of $R^1$ and one of $R^2$ in combination is:

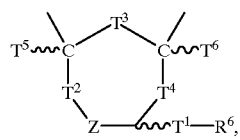

wherein $R^6$ is

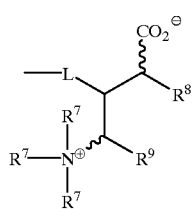

wherein L is O, S or $NR^{10}$, and wherein each $R^7$ independently is hydrogen or an unsaturated or saturated branched or unbranched aliphatic or alicyclic group having from 1 to 6 carbon atoms, and optionally at least one hetero atom, wherein $R^{10}$ independently is hydrogen or an unsaturated or saturated branched or unbranched aliphatic or alicyclic group having from 1 to 6 carbon atoms, and optionally at least one hetero atom, wherein each of $R^8$ and $R^9$ independently is hydrogen or an unsaturated or saturated branched or unbranched aliphatic or alicyclic group having from 1 to 50 carbon atoms, and optionally at least one hetero atom, or $R^8$ or $R^9$ in combination is

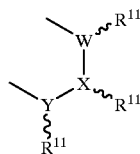

wherein each of W, X and Y independently is $(CR^{12})p$, O, S, or N, wherein $R^{11}$ independently is a lone pair of electrons $NR^{12}R^{13}$, $OR^{12}$, $SR^{12}$ or a hydrogen or an unsaturated or saturated branched or unbranched aliphatic or alicyclic group having from 1 to 50 carbon atoms, and optionally at least one hetero atom, wherein p is an integer of from 0 to 2, wherein each of $T^1$, $T^2$, $T^3$ and $T^4$ independently is an unsaturated branched or saturated branched or unbranched aliphatic or alicyclic group having 1 to 50 carbon atoms, and optionally includes at least one hetero atom, or is, or is in combination with $(C^{12}R^{13})_t$,

C=$NR^{13}$, $NR^{13}$, O, S, S=O, $SO_2$,

and wherein Z is $(CR^{12}CR^{13})_n$, $$\overset{O}{\underset{C,}{\|}} \quad \overset{S}{\underset{C,}{\|}}$$

C=$NR^{13}$, $NR^{13}$, O, S, S=O, $SO_2$, or a pair of terminating hydrogens, wherein each of $T^5$, $T^6$, $R^{12}$, and $R^{13}$ independently is hydrogen or an unsaturated or saturated branched or unbranched aliphatic or alicyclic group having from 1 to 50 carbon atoms, and optionally at least one hetero atom, and wherein each of n and t independently is an integer of from 0 to 20, and wherein $R^3$ is $R^6$, $T^1$—$R^6$, $R3^1A$, $OR^{14}$, $SR^{14}$ or a halide selected from the group consisting of chloro, fluoro, bromo, and iodo wherein $R^4$ is $R^6$, $T^1$—$R^6$, $R3^2A$, $OR^{15}$, $SR^{15}$ or a halide selected from the group consisting of chloro, fluoro, bromo, and iodo, wherein each of $R^{14}$ and $R^{15}$ independently is an unsaturated or saturated branched or unbranched aliphatic or alicyclic hetero or nonhetero group having 1 to 50 carbon atoms, and optionally at least one hetero atom, or $R^{14}$ and $R^{15}$ in combination is

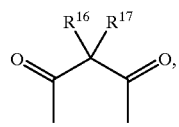

wherein each of $R^{16}$ and $R^{17}$ independently is hydrogen or an unsaturated or saturated branched or unbranched aliphatic and alicyclic group having 1 to 7 carbon atoms, or $R^{16}$ and $R^{17}$ in combination is a cyclic aliphatic hetero or nonhetero group having 2 to 7 carbon atoms and optionally at least one hetero atom, and wherein M is selected from the group consisting of Pt, V, Mo, W, Mn, Tc, Fe, Ru, Co, Rh, Ni, Pd, Cu, Au, and Zn.

6. The compound according to claim 5 wherein $R^5$ has 1 to 8 carbon atoms.

7. The compound according to claim 5 wherein $R^5$ has 1 to 5 carbons atoms.

8. The compound according to claim 5 wherein $R^7$ has 1 to 3 carbon atoms.

9. The compound according to claim 5 wherein t is an integer of from 0 to 3.

10. The compound according to claim 5 wherein at least one of $R^8$ or $R^9$ has from 5 to 25 carbon atoms.

11. The compound according to claim 5 wherein at least one of $R^8$ or $R^9$ has from 6 to 15 carbon atoms.

12. The compound according to claim 5 wherein $R^{10}$ has from 5 to 25 carbon atoms.

13. The compound according to claim 5 wherein $R^{10}$ has from 6 to 15 carbon atoms.

14. The compound according to claim 5 wherein p is 1.

15. The compound according to claim 5 wherein n is an integer of from 1 to 8.

16. The compound according to claim 5 wherein n is an integer of from 1 to 5.

17. The compound according to claim 5 wherein $R^{11}$ has from 5 to 25 carbon atoms.

18. The compound according to claim 5 wherein $R^{11}$ has from 6 to 15 carbon atoms.

19. The compound according to claim 5 wherein at least one of $R^{12}$ or $R^{13}$ has from 1 to 5 carbon atoms.

20. The enantiopure targeted drug agent having the structure:

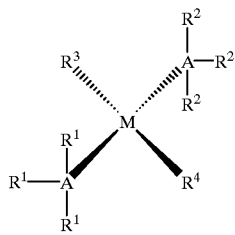

wherein each A independently is N, O, P, S or a halide selected from the group consisting of chloro, fluoro, bromo and iodo, and wherein each of $R^1$ and $R^2$ independently is a lone pair of electrons or hydrogen on $R^5$, wherein $R^5$ is an unsaturated or saturated branched or unbranched aliphatic or alicyclic group having 1 to 50 carbon atoms, and optionally at least one hetero atom with the proviso that either $R^3$ or $R^4$ independently is $R^6$ or at least one of $R^1$ or $R^1$ or $T^1$—$R^6$, wherein R6 is

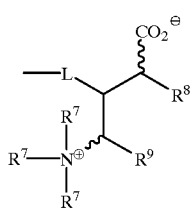

wherein L is O, S or $NR^{10}$, and wherein each $R^7$ is hydrogen or an unsaturated or saturated branched or unbranched aliphatic or alicyclic group having from 1 to 6 carbon atoms, and optionally at least one hetero atom, wherein $R^{10}$ independently is hydrogen or an unsaturated or saturated branched or unbranched aliphatic or alicyclic group having from 1 to 6 carbon atoms and optionally at least one hetero atom, wherein each of $R^8$ and $R^9$ independently is hydrogen or an unsaturated or saturated branched or unbranched aliphatic or alicyclic group having from one to 50 carbon atoms, and optionally at least one hetero atom, or $R^8$ or $R^9$ in combination is

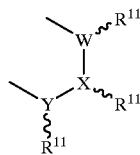

wherein each of W, X, and Y independently is $(CR^{12})_p$, O, S, or N, wherein each $R^{11}$ independently is a lone pair of electrons, $NR^{12}R^{13}$, $OR^{12}$, $SR^{12}$ or a hydrogen or an unsaturated or saturated branched or unbranched aliphatic or alicyclic group having from 1 to 50 carbon atoms, and optionally at least one hetero atom, wherein p is an integer of from 0 to 2, wherein $T^1$ is an unsaturated branched or saturated branched or unbranched aliphatic or alicyclic group having 1 to 50 carbon atoms, and optionally includes at least one hetero atom, or is in combination with, $(CR^{12}R^{13})_p$,

$C=NR^{13}$, $NR^{13}$, O, S, S=O, $SO_2$,

and wherein each of $R^{12}$ and $R^{13}$ independently is hydrogen or an unsaturated or saturated branched or unbranched aliphatic or alicyclic group having from 1 to 50 atoms, wherein t is an integer from 0 to 20, preferably 0 to 8 and most preferably 0 to 5, and wherein $R^3$ is $R^6$, $T^1$—$R^6$, R13A, $OR^{14}$, $SR^{14}$, or a halide selected from the group consisting of chloro, fluoro, bromo and iodo
wherein $R^4$ is $R^6$, $T^1$—$R^6$, $R3^2A$, $OR^{15}$, $SR^{15}$ or a halide selected from the group consisting fluoro, bromo and iodo, wherein each of $R^{14}$ and $R^{15}$ independently is an unsaturated or saturated branched or unbranched aliphatic or alicyclic hetero or nonhetero group having 1 to 50 carbon atoms, and optionally at least one hetero atom, or $R^{14}$ and $R^{15}$ in combination is

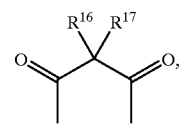

wherein each of $R^{16}$ and $R^{17}$ independently is hydrogen or an unsaturated or saturated branched or unbranched aliphatic or alicyclic group having 1 to 7 carbon atoms, or $R^{16}$ and $R^{17}$ combination is a cyclic aliphatic hetero or nonhetero group having 2 to 7 carbon atoms and optionally at least one hetero atom, and wherein M is selected from the group consisting of Pt, V, Mo, W, Mn, Tc, Fe, Ru, Co, Rh, Ni, Pd, Cu, Au, and Zn.

21. The compound according to claim 20 wherein $R^5$ has 1 to 8 carbon atoms.

22. The compound according to claim 20 wherein $R^5$ has 1 to 5 carbons atoms.

23. The compound according to claim 20 wherein $R^7$ has 1 to 3 carbon atoms.

24. The compound according to claim 20 wherein at least one of $R^8$ or $R^9$ has from 5 to 25 carbon atoms.

25. The compound according to claim 20 where in at least one of $R^8$ or $R^9$ has from 6 to 15 carbon atoms.

26. The compound according to claim 20 wherein $R^{10}$ has from 5 to 25 carbon atoms.

27. The compound according to claim 20 wherein $R^{10}$ has from 6 to 15 carbon atoms.

28. The compound according to claim 20 wherein p is 1.

29. The compound according to claim 20 wherein t is 0 to 3.

30. The compound according to claim 20 wherein n is an integer of from 1 to 8.

31. The compound according to claim 20 wherein n is an integer of from 1 to 5.

32. The compound according to claim 20 wherein $R^{11}$ has from 5 to 25 carbon atoms.

33. The compound according to claim 20 wherein at least one of $R^{12}$ or $R^{13}$ has from 1 to 5 carbon atoms.

34. The enantiopure targeted drug agent having the same structure:

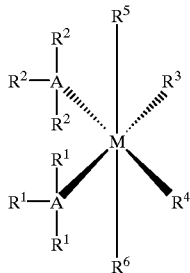

wherein each A independently is N, O, P, S or a halide selected from the group consisting of chloro, fluoro, bromo and iodo, and wherein each of $R^1$ and $R^2$ independently is a lone pair of electrons or hydrogen or $R^7$, wherein $R^7$ is an unsaturated or saturated branched or unbranched aliphatic or alicyclic group having 1 to 50 carbon atoms, and optionally at least one hetero atom with the proviso that either $R^3$, $R^4$, $R^5$ or $R^6$ indepently or in combination is $R^8$ or at least one of $R^1$ or $R^2$ is $T^1$—$R^8$, or one of $R^1$ and one of $R^2$ in combination is

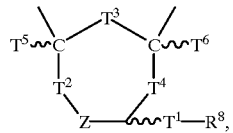

wherein $R^8$ is

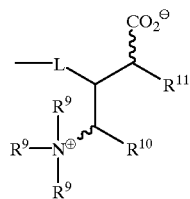

wherein L is O, S, or $NR^{12}$, and wherein each $R^9$ independently is hydrogen or an unsaturated or saturated branched or unbranched aliphatic or alicyclic group having from 1 to 6 carbon atoms, and optionally at least one hetero atom, wherein $R^{12}$ is hydrogen or an unsaturated or saturated branched or unbranched aliphatic or alicyclic group having from 1 to 6 carbon atoms, and optionally at least one hetero atom, wherein each of $R^{10}$ and $R^{11}$ independently is hydrogen or an unsaturated or saturated branched or unbranched aliphatic or alicyclic group having from one to 50 carbon atoms, and optionally at least one hetero atom, or $R^{10}$ and $R^{11}$ in combination is

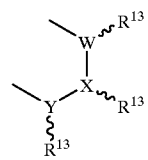

wherein each of W, X and Y independently is $(CR^{14})_p$, O, S, or N, wherein each $R^{13}$ independently is a lone pair of electrons, $NR^{14}R^{15}$, $OR^{14}$, $SR^{14}$ or a hydrogen or an unsaturated or saturated branched or unbranched aliphatic or alicyclic group having from 1 to 50 carbon atoms, and optionally at least one hetero atom, wherein p is an integer of from 1 to 2, wherein each of $T^1$, $T^2$, $T^3$ and $T^4$ independently is an unsaturated branched or saturated branched or unbranched aliphatic or alicyclic group having 1 to 50 carbon atoms, and optionally includes at least one hetero atom, or is, in combination with, $(CR^{12}R^{13})_p$,

$C=NR^{13}$, $NR^{13}$, O, S, S=O, $SO_2$,

and wherein Z is $(CR^{14}R^{15})_n$,

$C=NR^{15}$, $NR^{15}$, O, S, S=O, $SO_2$, or a pair of terminating hydrogens, wherein each of $T^5$, $T^6$, $R^{14}$ and $R^{15}$ independently is hydrogen or an unsaturated or saturated branched or unbranched aliphatic or alicyclic group having from 1 to 50 carbon atoms, and optionally at least one hetero atom, and wherein each of n and t independently is an integer of from 0 to 20, and wherein $R^3$ is $R^8$, $T^1$—$R^8$, $R3^1A$, $OR^{16}$, $SR^{16}$ or a halide selected from the group consisting of chloro, fluoro, bromo, iodo wherein $R^4$ is $R^8$, $T^1$—$R^8$, $R3^2A$, $OR^{17}$, $SR^{17}$ or a halide selected from the group consisting of chloro, fluoro, bromo, iodo, wherein $R^5$ is $R^8$, $T^1$—$R^8$, $R3^1A$, $OR^{16}$, $SR^{16}$ or a halide selected from the group consisting of chloro, fluoro, bromo, iodo wherein $R^6$ is $R^8$, $T^1$—$R^8$, $R3^2A$ $OR^{17}$, $SR^{17}$ or a halide selected from the group consisting of chloro, fluoro, bromo, iodo wherein each $R^{16}$ and $R^{17}$ independently is an unsaturated or saturated branched or unbranched aliphatic or alicyclic hetero or nonhetero group having 1 to 50 carbon atoms, and optionally at least one hetero atom, or $R^{16}$ and $R^{17}$ in combination is

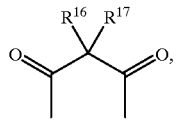

wherein each of $R^{18}$ and $R^{19}$ independently is hydrogen or an unsaturated or saturated branched or unbranched aliphatic or alicyclic group having 1 to 7 carbon atoms, or R18 and $R^{19}$ combination in a cyclic aliphatic hetero or nonhetero group having 2 to 7 carbon atoms and optionally at least one hetero atom, and wherein M is selected from the group consisting of Pt, V, Mo, W, Mn, Tc, Fe, Ru, Co, Rh, Ni, Pd, Cu, Au and Zn.

35. An enantiopure targeted drug agent having the structure:

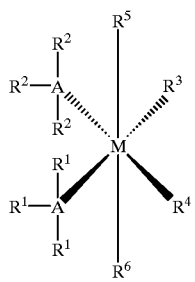

wherein each of A independently is N, O, P, S or a halide selected from the group chloro, fluoro, bromo and iodo, and wherein each of $R^1$ and $R^2$ independently is a lone pair of electrons or hydrogen or $R^7$, wherein $R^7$ is an unsaturated or saturated branched or unbranched aliphatic or alicyclic group having 1 to 50 carbon atoms, and optionally at least one hetero atom with the proviso that either $R^3$, $R^4$, $R^5$ or $R^6$ independently or in combination is $R^8$ or at least one of $R^1$ or $R^2$ is $T^1$—$R^8$, or one of $R^1$ and one of $R^2$ in combination is

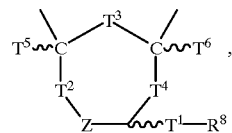

wherein $R^8$ is

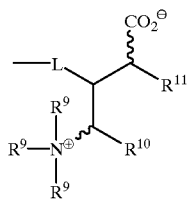

wherein L is O, S or $NR^{12}$, and wherein $R^9$ independently is hydrogen or an unsaturated or saturated branched or unbranched aliphatic or alicyclic group having from 1 to 6 carbon atoms, and optionally at least one hetero atom, wherein $R^{12}$ independently is hydrogen or an unsaturated or saturated branched or unbranched aliphatic or alicyclic group having from 1 to 6 carbon atoms, and optionally at least one hetero atom, wherein $R^{10}$ and $R^{11}$ independently is hydrogen or an unsaturated or saturated branched or unbranched aliphatic or alicyclic group having from one to 50 carbon atoms, and optionally at least one hetero atom, or $R^{10}$ and $R^{11}$ in combination is

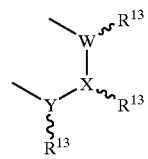

wherein each of W, X and Y independently is $(CR^{14})_p$, O, S, or N, wherein $R^{13}$ independently is a lone pair of electrons, $NR^{14}R^{15}$, $OR^{14}$, $SR^{14}$ or a hydrogen or an unsaturated or saturated branched or unbranched aliphatic or alicyclic group having from 1 to 50 carbon atoms, and optionally at least one hetero atom, wherein p is an integer of from 0 to 2, wherein each of $T^1$, $T^2$, $T^3$ and $T^4$ independently is an unsaturated branched or saturated branched or unbranched aliphatic or alicyclic group having 1 to 50 carbon atoms, and optionally includes at least one hetero atom, or is, or is in combination with, $(CR^{12}R^{13})_t$,

$C=NR^{13}$, $NR^3$, O, S, S=O, $SO_2$,

and wherein Z is $(CR^{14}R^{15})_n$,

$C=NR^{15}$, O, S, S=O, $SO_2$, or a pair of terminating hydrogens, wherein each of $T^5$, $T^6$, $R^{14}$ and $R^{15}$ independently is hydrogen or an unsaturated or saturated branched or unbranched aliphatic or alicyclic group having from 1 to 50 carbon atoms, and optionally at least one hetero atom, and wherein each of n and t independently is an integer of from 0 to 20, and wherein $R^3$ is $R^8$, $T^1$—$R^8$, $R_3^1A$, $OR^{16}$, $SR^{16}$ or a halide selected from the group consisting of chloro, fluoro, bromo, and iodo wherein $R^4$ is $R^8$, $T^1$—$R^8$, $R_3^2A$, $OR^{17}$, $SR^{17}$ or a halide selected from the group consisting of chloro, fluoro, bromo, and iodo, wherein $R^5$ is $R^8$, $T^1$—$R^8$, $R_3^1A$, $OR^{16}$, $SR^{16}$ or a halide selected from the group consisting of chloro, fluoro, bromo, and iodo, wherein $R^6$ is $R^8$, $T^1$—$R^8$, $R_3^2A$, $OR^{17}$, $SR^{17}$ or a halide selected from the group consisting of chloro, fluoro, bromo, and iodo, wherein each of $R^{16}$ and $R^{17}$ independently is an unsaturated or saturated branched or unbranched aliphatic or alicyclic hetero or nonhetero group having 1 to 50 carbon atoms, and optionally at least one hetero atom, or $R^{16}$ and $R^{17}$ in combination is

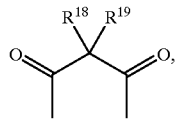

wherein each of $R^{18}$ and $R^{19}$ independently is hydrogen or an unsaturated or saturated branched or unbranched aliphatic or alicyclic group having 1 to 7 carbon atoms, or $R^{18}$ and $R^{19}$ in combination is a cyclic aliphatic hetero or nonhetero group having 2 to 7 carbon atoms and optionally at least one hetero atom, and wherein M is selected from the group consisting of Pt, V, Mo, W, Mn, Tc, Fe, Ru, Co, Rh, Ni, Pd, Cu, Au, and Zn.

36. The compound according to claim 35 wherein $R^5$ has 1 to 8 carbon atoms.

37. The compound according to claim 35 wherein $R^5$ has 1 to 5 carbons atoms.

38. The compound according to claim 35 wherein $R^7$ has 0 to 3 carbon atoms.

39. The compound according to claim 35 where in at least on of $R^8$ or $R^9$ has from 5 to 25 carbon atoms.

40. The compound according to claim 35 wherein $R^8$ or $R^9$ have from 5 to 25 carbon atoms.

41. The compound according to claim 35 wherein at least one of $R^8$ or $R^9$ has from 6 to 15 carbon atoms.

42. The compound according to claim 35 wherein $R^{10}$ has from 5 to 25 carbon atoms.

43. The compound according to claim 35 wherein $R^{10}$ has from 6 to 15 carbon atoms.

44. The compound according to claim 35 wherein p is 1.

45. The compound according to claim 35 wherein n is an integer of from 1 to 8.

46. The compound according to claim 35 wherein n is an integer of from 1 to 5.

47. The compound according to claim 35 wherein $R^{11}$ has from 5 to 25 carbon atoms.

48. The compound according to claim 35 wherein $R^{11}$ has from 6 to 15 carbon atoms.

49. The compound according to claim 35 wherein $R^{12}$ or $R^{13}$ have from 1 to 5 carbon atoms.

50. An enantiopure targeted drug agent having the structure:

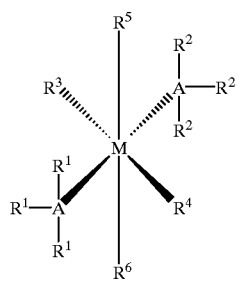

wherein each A independently is N, O, P, S, or a halide selected from the group consisting of chloro, fluoro, bromo, and iodo, and where in each of $R^1$ and $R^2$ independently is a lone pair of electrons or hydrogen of $R^7$, wherein $R^7$ is an unsaturated or saturated branched or unbranched aliphatic or alicyclic group having 1 to 50 carbon atoms, and optionally at least one hetero atom with the proviso that either $R^3$, $R^4$, $R^5$ or $R^6$ independently or in combination is $R^8$ or at least one of $R^1$ or $R^2$ is $T^1$—$R^8$, wherein

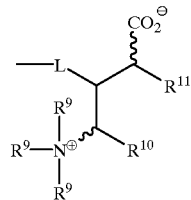

wherein L is O, S or $NR^{12}$, and wherein each $R^9$ independently is hydrogen or an unsaturated or saturated branched or unbranched aliphatic or alicyclic group having from 1 to 6 carbon atoms, and optionally at least one hetero atom, wherein $R^{12}$ is hydrogen or an unsaturated or saturated branched or unbranched aliphatic or alicyclic group having from 1 to 6 carbon atoms, and optionally at least one hetero atom, wherein each of $R^{10}$ and $R^{11}$ independently is hydrogen or an unsaturated or saturated branched or unbranched aliphatic or alicyclic group having one to 50 carbon atoms, and optionally at least one hetero atom, or $R^{10}$ and $R^{11}$ in combination is

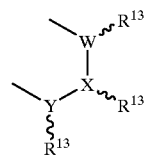

wherein each of W, X and Y independently is $(C^{14})_p$, O, S, or N, wherein each $R^{13}$ independently is a lone pair of electrons, $NR^{14}R^{15}$, $OR^{14}$, $SR^{14}$ or a hydrogen or an unsaturated or saturated branched or unbranched aliphatic or alicyclic group having 1 to 50 carbon atoms, and optionally at least one hetero atom, wherein p is an integer of from 0 to 2, wherein $T^1$ is an unsaturated or saturated branched or unbranched aliphatic or alicyclic group having 1 to 50 carbon atoms, and optionally includes a least one hetero atom, or is, in combination with, $(CR^{12}R^{13})_p$,

C=$NR^{13}$, $NR^{13}$, O, S, S=O, $SO_2$,

wherein each $R^{14}$ and $R^{15}$ independently is hydrogen or an unsaturated or saturated branched or unbranched aliphatic or alicyclic group having 1 to 50 carbon atoms, wherein t is an integer from 0 to 20, and wherein $R^3$ is $R^8$, $T^1$—$R^8$, $R3^1A$, $OR^{16}$, $SR^{16}$ or a halide selected from the group consisting of chloro, fluoro, bromo and iodo wherein $R^4$ is $R^8$, $T^1$—$R^8$, $R3^2A$, $OR^{17}$, $SR^{17}$ or a halide selected from the group consisting of chloro, fluoro, bromo and iodo wherein $R^5$ is $R^8$, $T^1$—$R^8$, $R3^1A$, $OR^{16}$, $SR^{16}$, or a halide selected from the group consisting of chloro, fluoro, bromo and iodo wherein $R^6$ is $R^8$, $T^1$—$R^8$, $R3^2A$, $OR^{17}$, $SR^{17}$ or a halide selected from the group consisting of chloro, fluoro, bromo and iodo wherein each of $R^{16}$ and $R^{17}$ independently is an unsaturated or saturated branched or unbranched aliphatic or alicyclic hetero or nonhetero group having 1 to 50 carbon atoms, and optionally at least one hetero atom, or $R^{16}$ and $R^{17}$ in combination is

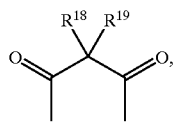

wherein each of $R^{18}$ and $R^{19}$ independently is hydrogen or an unsaturated or saturated branched or unbranched aliphatic or alicyclic group having 1 to 7 carbon atoms, or $R^{18}$ and $R^{19}$ in combination is a cyclic aliphatic hetero or nonhetero group having 2 to 7 carbon atoms and optionally at least one hetero atom, and wherein M is selected from the group consisting of Pt, V, Mo, W, Mn, Tc, Fe, Ru, Co, Rh, Ni, Pd, Cu, Au, and Zn.

51. The compound according to claim 50 wherein $R^5$ has 1 to 8 carbon atoms.

52. The compound according to claim 50 wherein $R^5$ has 1 to 5 carbons atoms.

53. The compound according to claim 50 wherein $R^7$ has 1 to 3 carbon atoms.

54. The compound according to claim 50 wherein at least one of $R^8$ or $R^9$ has from 5 to 25 carbon atoms.

55. The compound according to claim 50 wherein at least one of $R^8$ or $R^9$ has from 6 to 15 carbon atoms.

56. The compound according to claim 50 wherein $R^{10}$ has from 5 to 25 carbon atoms.

57. The compound according to claim 50 wherein $R^{10}$ has from 6 to 15 carbon atoms.

58. The compound according to claim 50 wherein p is 1.

59. The compound according to claim 50 wherein t is 0 to 3.

60. The compound according to claim 50 wherein n is an integer of from 1 to 8.

61. The compound according to claim 50 wherein n is an integer of from 1 to 5.

62. The compound according to claim 50 wherein $R^{11}$ has from 5 to 25 carbon atoms.

63. The compound according to claim 50 wherein $R^{11}$ has from 6 to 15 carbon atoms.

64. The compound according to claim 50 wherein $R^{12}$ or $R^{13}$ have from 1 to 5 carbon atoms.

65. A method for treating neoplastic disorders comprising administering an effective amount of the compound of claim 5 to a subject, with the proviso that M is Pt.

66. A method for treating neoplastic disorders comprising administering an effective amounts of the compound of claim 20 to a subject, with the proviso that M is Pt.

67. A method for treating neoplastic disorders comprising administering an effective amount of the compound of claim 35 to a subject, with the proviso that M is Pt.

68. A method for treating neoplastic disorders comprising administering an effective amount of the compound of claim 50 to a subject, with the proviso that M is Pt.

69. A method for treating arthritic disorders in a subject comprising administering an effective amount of the compound of claim 5 to a subject, with the proviso that M is Au.

70. A method for treating arthritic disorders in a subject comprising administering an effective amount of the compound of claim 20 to a subject, with the proviso that M is Au.

71. The compound of claim 5, wherein said compound has the structure:

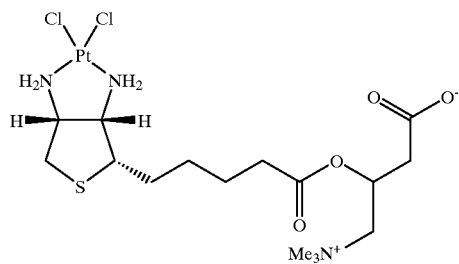

* * * * *